(12) United States Patent
O'Halloran et al.

(10) Patent No.: US 9,220,554 B2
(45) Date of Patent: *Dec. 29, 2015

(54) METHODS AND APPARATUS FOR TREATING VERTEBRAL FRACTURES

(75) Inventors: Damien O'Halloran, King of Prussia, PA (US); Sean Suh, Plymouth Meeting, PA (US)

(73) Assignee: Globus Medical, Inc., Audubon, PA (US)

( * ) Notice: Subject to any disclaimer, the term of this patent is extended or adjusted under 35 U.S.C. 154(b) by 631 days.

This patent is subject to a terminal disclaimer.

(21) Appl. No.: 12/708,233

(22) Filed: Feb. 18, 2010

(65) Prior Publication Data

US 2011/0202062 A1  Aug. 18, 2011

(51) Int. Cl.
| | |
|---|---|
| A61B 17/56 | (2006.01) |
| A61B 17/88 | (2006.01) |
| A61B 17/70 | (2006.01) |
| A61B 17/16 | (2006.01) |
| A61B 17/34 | (2006.01) |

(52) U.S. Cl.
CPC .......... *A61B 17/8855* (2013.01); *A61B 17/7097* (2013.01); *A61B 17/8852* (2013.01); *A61B 17/1671* (2013.01); *A61B 17/3472* (2013.01); *A61B 2017/3445* (2013.01); *A61B 2017/3454* (2013.01)

(58) Field of Classification Search
CPC ........... A61B 17/8855; A61B 17/7097; A61B 17/8852; A61F 2/4601
USPC .............................. 606/92, 93, 94; 623/17.12
See application file for complete search history.

(56) References Cited

U.S. PATENT DOCUMENTS

| | | | |
|---|---|---|---|
| 4,969,888 | A | 11/1990 | Scholten et al. |
| 5,108,404 | A | 4/1992 | Scholten |
| 5,445,639 | A | 8/1995 | Kuslich |
| 5,549,679 | A | 8/1996 | Kuslich |
| 5,571,189 | A | 11/1996 | Kuslich |
| 5,827,289 | A | 10/1998 | Reiley |
| 5,972,015 | A | 10/1999 | Scribner et al. |

(Continued)

FOREIGN PATENT DOCUMENTS

WO  9902214  1/1999

OTHER PUBLICATIONS

U.S. Appl. No. 08/188,224 Mark A. Reiley, filed Jan. 26, 1994 Inflatable Device for Use in Surgical Protocol Relating to a Fixation of Bone.

(Continued)

*Primary Examiner* — Zade Coley

(57) ABSTRACT

Methods and apparatus for treating bones, including, in one or more embodiments, methods and apparatus for treatment of vertebral fractures that include a containment assembly for cement containment and/or a balloon assembly for maintaining vertebral height. Methods for treating a bone comprising: inserting a cannula having an inner lumen into the bone; creating a cavity in the bone; providing a containment assembly, wherein the containment assembly may comprise a tubular member having a proximal end and a distal end, a containment jacket disposed on the distal end of the tubular member, and a guide wire disposed through the tubular member with the guide extending into the containment jacket; inserting the containment jacket through the inner lumen of the cannula and into the cavity; and introducing a filler material into the containment jacket.

14 Claims, 13 Drawing Sheets

(56) References Cited

U.S. PATENT DOCUMENTS

| | | | |
|---|---|---|---|
| 6,048,346 A | 4/2000 | Reiley et al. | |
| 6,066,154 A | 5/2000 | Reiley et al. | |
| 6,235,043 B1 | 5/2001 | Reiley et al. | |
| 6,241,734 B1 | 6/2001 | Scribner et al. | |
| 6,248,110 B1* | 6/2001 | Reiley et al. | 606/93 |
| 6,280,456 B1 | 8/2001 | Scribner et al. | |
| 6,423,083 B2 | 7/2002 | Reiley | |
| 6,440,138 B1 | 8/2002 | Reiley | |
| 6,468,279 B1 | 10/2002 | Reo | |
| 6,558,390 B2 | 5/2003 | Cragg | |
| 6,575,919 B1 | 6/2003 | Reiley | |
| 6,595,998 B2 | 7/2003 | Johnson | |
| 6,607,544 B1 | 8/2003 | Boucher et al. | |
| 6,613,054 B2 | 9/2003 | Scribner et al. | |
| 6,620,162 B2 | 9/2003 | Kuslich | |
| 6,623,505 B2 | 9/2003 | Scribner et al. | |
| 6,632,235 B2 | 10/2003 | Weikel et al. | |
| 6,641,587 B2 | 11/2003 | Scribner | |
| 6,645,213 B2 | 11/2003 | Sand et al. | |
| 6,663,647 B2 | 12/2003 | Reiley | |
| 6,676,665 B2 | 1/2004 | Foley et al. | |
| 6,706,069 B2 | 3/2004 | Berger | |
| 6,716,216 B1 | 4/2004 | Boucher et al. | |
| 6,719,761 B1 | 4/2004 | Reiley et al. | |
| 6,719,773 B1 | 4/2004 | Boucher et al. | |
| 6,726,691 B2 | 4/2004 | Osorio et al. | |
| 6,740,093 B2 | 5/2004 | Hochschuler | |
| 6,805,697 B1 | 10/2004 | Helm | |
| 6,814,736 B2 | 11/2004 | Reiley et al. | |
| 6,863,672 B2 | 3/2005 | Reiley | |
| 6,869,445 B1 | 3/2005 | Johnson | |
| 6,875,212 B2* | 4/2005 | Shaolian et al. | 606/86 A |
| 6,899,719 B2 | 5/2005 | Reiley | |
| 6,923,813 B2 | 8/2005 | Phillips et al. | |
| 6,932,843 B2 | 8/2005 | Smith et al. | |
| 6,960,215 B2 | 11/2005 | Olson, Jr. | |
| 6,979,341 B2 | 12/2005 | Scribner et al. | |
| 6,981,981 B2 | 1/2006 | Reiley | |
| 6,997,929 B2 | 2/2006 | Manzi | |
| 7,014,633 B2 | 3/2006 | Cragg | |
| 7,044,954 B2 | 5/2006 | Reiley | |
| 7,063,703 B2 | 6/2006 | Reo | |
| 7,081,122 B1 | 7/2006 | Reiley | |
| 7,114,501 B2 | 10/2006 | Johnson et al. | |
| 7,153,305 B2 | 12/2006 | Johnson | |
| 7,153,306 B2 | 12/2006 | Ralph | |
| 7,153,307 B2 | 12/2006 | Scribner et al. | |
| 7,156,861 B2 | 1/2007 | Scribner et al. | |
| 7,160,306 B2 | 1/2007 | Matsuzaki | |
| 7,175,627 B2 | 2/2007 | Lin et al. | |
| 7,175,628 B2 | 2/2007 | Lin et al. | |
| 7,175,629 B2 | 2/2007 | Lin et al. | |
| 7,226,481 B2 | 6/2007 | Kuslich | |
| 7,234,468 B2 | 6/2007 | Johnson | |
| 7,241,303 B2 | 7/2007 | Reiss et al. | |
| 7,252,671 B2 | 8/2007 | Scribner | |
| 7,252,686 B2 | 8/2007 | Carrison | |
| 7,261,720 B2 | 8/2007 | Stevens | |
| 7,309,324 B2 | 12/2007 | Hayes et al. | |
| 7,309,338 B2 | 12/2007 | Cragg | |
| 7,311,713 B2 | 12/2007 | Johnson | |
| 7,354,419 B2 | 4/2008 | Davies, Jr. et al. | |
| 7,399,306 B2 | 7/2008 | Reiley | |
| 7,465,318 B2 | 12/2008 | Sennett et al. | |
| 7,488,337 B2 | 2/2009 | Saab et al. | |
| 7,500,992 B2 | 3/2009 | Li | |
| 7,507,241 B2 | 3/2009 | Levy | |
| 7,513,900 B2 | 4/2009 | Carrison | |
| 7,520,888 B2 | 4/2009 | Trieu | |
| 7,544,196 B2 | 6/2009 | Bagga | |
| 7,547,317 B2 | 6/2009 | Cragg | |
| 7,559,932 B2 | 7/2009 | Truckai et al. | |
| 7,909,827 B2 | 3/2011 | Reiley | |
| 2001/0011174 A1 | 8/2001 | Reiley | |
| 2002/0026195 A1 | 2/2002 | Layne et al. | |
| 2002/0068974 A1 | 6/2002 | Kuslich | |
| 2002/0198526 A1* | 12/2002 | Shaolian et al. | 606/61 |
| 2003/0032963 A1 | 2/2003 | Reiss et al. | |
| 2003/0050644 A1* | 3/2003 | Boucher et al. | 606/90 |
| 2003/0088249 A1* | 5/2003 | Furderer | 606/61 |
| 2003/0105469 A1 | 6/2003 | Karmon | |
| 2003/0130664 A1 | 7/2003 | Boucher et al. | |
| 2003/0171812 A1 | 9/2003 | Grunberg | |
| 2003/0191489 A1 | 10/2003 | Reiley | |
| 2003/0220648 A1 | 11/2003 | Osorio et al. | |
| 2003/0220650 A1 | 11/2003 | Major | |
| 2003/0229372 A1 | 12/2003 | Reiley et al. | |
| 2004/0010263 A1 | 1/2004 | Boucher et al. | |
| 2004/0019354 A1 | 1/2004 | Johnson et al. | |
| 2004/0024410 A1 | 2/2004 | Olson, Jr. et al. | |
| 2004/0049202 A1 | 3/2004 | Berger | |
| 2004/0098015 A1* | 5/2004 | Weikel et al. | 606/192 |
| 2004/0153064 A1 | 8/2004 | Foley et al. | |
| 2004/0153115 A1 | 8/2004 | Reiley | |
| 2004/0167562 A1 | 8/2004 | Osorio et al. | |
| 2004/0186481 A1* | 9/2004 | Chern Lin et al. | 606/92 |
| 2004/0210297 A1 | 10/2004 | Lin et al. | |
| 2004/0215343 A1 | 10/2004 | Hochschuler | |
| 2004/0215344 A1 | 10/2004 | Hochschuler | |
| 2004/0220580 A1 | 11/2004 | Johnson | |
| 2004/0220672 A1 | 11/2004 | Shadduck et al. | |
| 2004/0230309 A1* | 11/2004 | DiMauro et al. | 623/17.12 |
| 2004/0249382 A1 | 12/2004 | Olson, Jr. | |
| 2004/0267271 A9* | 12/2004 | Scribner et al. | 606/92 |
| 2005/0010297 A1 | 1/2005 | Watson et al. | |
| 2005/0015140 A1 | 1/2005 | deBeer | |
| 2005/0015148 A1 | 1/2005 | Jansen | |
| 2005/0038514 A1 | 2/2005 | Helm | |
| 2005/0043737 A1 | 2/2005 | Reiley | |
| 2005/0055097 A1 | 3/2005 | Grunberg | |
| 2005/0080425 A1 | 4/2005 | Bhatnagar | |
| 2005/0090852 A1 | 4/2005 | Layne | |
| 2005/0119662 A1* | 6/2005 | Reiley et al. | 606/92 |
| 2005/0171552 A1 | 8/2005 | Johnson | |
| 2005/0182412 A1 | 8/2005 | Johnson | |
| 2005/0182414 A1 | 8/2005 | Manzi | |
| 2005/0182417 A1 | 8/2005 | Pagano | |
| 2005/0187559 A1 | 8/2005 | Raymond et al. | |
| 2005/0209595 A1 | 9/2005 | Karmon | |
| 2005/0209629 A1 | 9/2005 | Kerr | |
| 2005/0234493 A1 | 10/2005 | Carr et al. | |
| 2005/0234498 A1 | 10/2005 | Gronemeyer et al. | |
| 2005/0240193 A1 | 10/2005 | Layne et al. | |
| 2005/0261683 A1 | 11/2005 | Veldhuizen | |
| 2005/0278023 A1 | 12/2005 | Zwirkoski | |
| 2005/0278036 A1 | 12/2005 | Leonard | |
| 2006/0004455 A1 | 1/2006 | Leonard | |
| 2006/0079905 A1 | 4/2006 | Beyar | |
| 2006/0085007 A1 | 4/2006 | Li | |
| 2006/0085009 A1 | 4/2006 | Truckai et al. | |
| 2006/0085024 A1 | 4/2006 | Pepper et al. | |
| 2006/0089715 A1 | 4/2006 | Truckai et al. | |
| 2006/0095064 A1 | 5/2006 | Scribner et al. | |
| 2006/0100635 A1 | 5/2006 | Reiley | |
| 2006/0100706 A1 | 5/2006 | Shadduck et al. | |
| 2006/0106459 A1 | 5/2006 | Truckai | |
| 2006/0106461 A1 | 5/2006 | Embry | |
| 2006/0116689 A1 | 6/2006 | Albans | |
| 2006/0116690 A1 | 6/2006 | Pagano | |
| 2006/0122614 A1 | 6/2006 | Truckai et al. | |
| 2006/0122621 A1 | 6/2006 | Truckai et al. | |
| 2006/0122622 A1 | 6/2006 | Truckai et al. | |
| 2006/0122624 A1 | 6/2006 | Truckai et al. | |
| 2006/0122625 A1 | 6/2006 | Truckai et al. | |
| 2006/0149268 A1 | 7/2006 | Truckai et al. | |
| 2006/0149379 A1 | 7/2006 | Kuslich | |
| 2006/0155296 A1 | 7/2006 | Richter | |
| 2006/0161166 A1 | 7/2006 | Johnson | |
| 2006/0182780 A1 | 8/2006 | Riley | |
| 2006/0184192 A1 | 8/2006 | Markworth et al. | |
| 2006/0184246 A1 | 8/2006 | Zwirkoski | |
| 2006/0195115 A1 | 8/2006 | Ferree | |
| 2006/0217736 A1 | 9/2006 | Kaneko | |
| 2006/0224241 A1 | 10/2006 | Butler | |

(56) References Cited

U.S. PATENT DOCUMENTS

| | | |
|---|---|---|
| 2006/0229625 A1 | 10/2006 | Truckai et al. |
| 2006/0229628 A1 | 10/2006 | Truckai et al. |
| 2006/0229629 A1 | 10/2006 | Manzi |
| 2006/0235338 A1 | 10/2006 | Pacheco |
| 2006/0235417 A1 | 10/2006 | Sala |
| 2006/0235423 A1 | 10/2006 | Cantu |
| 2006/0235460 A1 | 10/2006 | Reiley et al. |
| 2006/0241627 A1 | 10/2006 | Reo |
| 2006/0241644 A1 | 10/2006 | Osorio et al. |
| 2006/0247648 A1 | 11/2006 | Serbousek |
| 2006/0264945 A1 | 11/2006 | Edidin et al. |
| 2006/0264965 A1 | 11/2006 | Shadduck et al. |
| 2006/0265077 A1 | 11/2006 | Zwirkoski |
| 2006/0271061 A1 | 11/2006 | Beyar |
| 2006/0276819 A1 | 12/2006 | Osorio et al. |
| 2007/0010844 A1 | 1/2007 | Gong et al. |
| 2007/0010845 A1 | 1/2007 | Gong et al. |
| 2007/0010848 A1 | 1/2007 | Leung |
| 2007/0021769 A1 | 1/2007 | Scribner et al. |
| 2007/0027230 A1 | 2/2007 | Beyar |
| 2007/0043373 A1 | 2/2007 | Sala |
| 2007/0043440 A1 | 2/2007 | William et al. |
| 2007/0049849 A1 | 3/2007 | Schwardt et al. |
| 2007/0049961 A1 | 3/2007 | Tsou |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055261 A1 | 3/2007 | Reiley |
| 2007/0055265 A1 | 3/2007 | Schaller |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller |
| 2007/0055275 A1 | 3/2007 | Schaller |
| 2007/0055276 A1* | 3/2007 | Edidin ............... 606/92 |
| 2007/0055280 A1 | 3/2007 | Osorio et al. |
| 2007/0055281 A1 | 3/2007 | Osorio et al. |
| 2007/0055283 A1 | 3/2007 | Scribner |
| 2007/0055284 A1 | 3/2007 | Osorio et al. |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0060924 A1 | 3/2007 | Choi |
| 2007/0060941 A1 | 3/2007 | Reiley et al. |
| 2007/0067034 A1 | 3/2007 | Chirico et al. |
| 2007/0073307 A1 | 3/2007 | Scribner |
| 2007/0088436 A1 | 4/2007 | Parsons |
| 2007/0093822 A1 | 4/2007 | Dutoit et al. |
| 2007/0093847 A1 | 4/2007 | Scribner |
| 2007/0093899 A1* | 4/2007 | Dutoit et al. ............ 623/17.11 |
| 2007/0112299 A1 | 5/2007 | Smit et al. |
| 2007/0118143 A1 | 5/2007 | Ralph |
| 2007/0123877 A1 | 5/2007 | Goldin |
| 2007/0123986 A1 | 5/2007 | Schaller |
| 2007/0129669 A1 | 6/2007 | Lin et al. |
| 2007/0129670 A1 | 6/2007 | Lin et al. |
| 2007/0142765 A1 | 6/2007 | Lin et al. |
| 2007/0149978 A1 | 6/2007 | Shezifi |
| 2007/0156242 A1 | 7/2007 | Lin et al. |
| 2007/0156251 A1 | 7/2007 | Karmon |
| 2007/0162032 A1 | 7/2007 | Johnson |
| 2007/0162127 A1 | 7/2007 | Peterman |
| 2007/0162132 A1 | 7/2007 | Messerli |
| 2007/0168038 A1 | 7/2007 | Trieu |
| 2007/0168039 A1 | 7/2007 | Trieu |
| 2007/0173826 A1 | 7/2007 | Canaveral |
| 2007/0197861 A1 | 8/2007 | Reiley |
| 2007/0197935 A1 | 8/2007 | Reiley |
| 2007/0198013 A1 | 8/2007 | Foley |
| 2007/0198020 A1 | 8/2007 | Reiley |
| 2007/0213732 A1 | 9/2007 | Khanna et al. |
| 2007/0213760 A1 | 9/2007 | Hayes |
| 2007/0213822 A1 | 9/2007 | Trieu |
| 2007/0213823 A1 | 9/2007 | Trieu |
| 2007/0219490 A1 | 9/2007 | Pepper |
| 2007/0219634 A1 | 9/2007 | Greenhalgh |
| 2007/0233146 A1 | 10/2007 | Henniges |
| 2007/0239162 A1 | 10/2007 | Bhatnagar |
| 2007/0244485 A1 | 10/2007 | Greenhalgh et al. |
| 2007/0282346 A1 | 12/2007 | Scribner |
| 2007/0299455 A1 | 12/2007 | Stevens |
| 2007/0299460 A9 | 12/2007 | Boucher et al. |
| 2008/0009792 A1 | 1/2008 | Henniges |
| 2008/0009868 A1 | 1/2008 | Gotfried |
| 2008/0021463 A1 | 1/2008 | Georgy |
| 2008/0027453 A1 | 1/2008 | Johnson |
| 2008/0027454 A1 | 1/2008 | Johnson |
| 2008/0033446 A1* | 2/2008 | Lin ............... 606/92 |
| 2008/0039854 A1 | 2/2008 | Rabiner |
| 2008/0046082 A1 | 2/2008 | Lee |
| 2008/0051707 A1 | 2/2008 | Phan |
| 2008/0051800 A1 | 2/2008 | Diaz |
| 2008/0051818 A1 | 2/2008 | Phan |
| 2008/0051819 A1 | 2/2008 | Chasmawala |
| 2008/0051820 A1 | 2/2008 | Gong et al. |
| 2008/0051825 A1 | 2/2008 | Reiley et al. |
| 2008/0058725 A1 | 3/2008 | Scribner |
| 2008/0058823 A1 | 3/2008 | Reiley et al. |
| 2008/0058824 A1 | 3/2008 | Reiley et al. |
| 2008/0058825 A1 | 3/2008 | Scribner |
| 2008/0058826 A1 | 3/2008 | Scribner |
| 2008/0058827 A1 | 3/2008 | Osorio et al. |
| 2008/0058828 A1 | 3/2008 | Reiley et al. |
| 2008/0058855 A1 | 3/2008 | Reiley |
| 2008/0058857 A1 | 3/2008 | Reiley |
| 2008/0058943 A1 | 3/2008 | Reiley |
| 2008/0065020 A1 | 3/2008 | Ralph |
| 2008/0065087 A1 | 3/2008 | Osorio et al. |
| 2008/0065089 A1 | 3/2008 | Osorio et al. |
| 2008/0065091 A1 | 3/2008 | Scribner |
| 2008/0065137 A1 | 3/2008 | Boucher et al. |
| 2008/0065138 A1 | 3/2008 | Reiley |
| 2008/0065139 A1 | 3/2008 | Scribner et al. |
| 2008/0065142 A1 | 3/2008 | Reiley |
| 2008/0065190 A1 | 3/2008 | Osorio et al. |
| 2008/0071283 A1 | 3/2008 | Osorio et al. |
| 2008/0086133 A1 | 4/2008 | Kuslich |
| 2008/0086142 A1 | 4/2008 | Kohm et al. |
| 2008/0091199 A1 | 4/2008 | Cragg |
| 2008/0103505 A1 | 5/2008 | Fransen |
| 2008/0103518 A1 | 5/2008 | Karmon |
| 2008/0114364 A1 | 5/2008 | Goldin |
| 2008/0132934 A1 | 6/2008 | Reiley |
| 2008/0132935 A1 | 6/2008 | Osorio et al. |
| 2008/0140079 A1 | 6/2008 | Osorio et al. |
| 2008/0140083 A1 | 6/2008 | Reiley et al. |
| 2008/0140084 A1 | 6/2008 | Osorio et al. |
| 2008/0154272 A1 | 6/2008 | Schaller |
| 2008/0154304 A1 | 6/2008 | Crawford |
| 2008/0172081 A1 | 7/2008 | Reiss et al. |
| 2008/0177259 A1 | 7/2008 | Wu |
| 2008/0183204 A1 | 7/2008 | Greenhalgh |
| 2008/0188805 A1 | 8/2008 | Davies |
| 2008/0195081 A1 | 8/2008 | Moll |
| 2008/0195112 A1 | 8/2008 | Liu |
| 2008/0195207 A1 | 8/2008 | Lin et al. |
| 2008/0215151 A1 | 9/2008 | Kohm et al. |
| 2008/0221505 A1 | 9/2008 | Betts |
| 2008/0221608 A1 | 9/2008 | Betts |
| 2008/0228284 A1 | 9/2008 | Fritz |
| 2008/0234687 A1 | 9/2008 | Schaller |
| 2008/0234827 A1 | 9/2008 | Schaller |
| 2008/0243122 A1 | 10/2008 | Kohm |
| 2008/0243249 A1 | 10/2008 | Kohm et al. |
| 2008/0249481 A1 | 10/2008 | Crainich et al. |
| 2008/0249604 A1 | 10/2008 | Donovan |
| 2008/0255569 A1 | 10/2008 | Kohm et al. |
| 2008/0255624 A1 | 10/2008 | Arcenio et al. |
| 2008/0269759 A1 | 10/2008 | Reiley et al. |
| 2008/0269760 A1 | 10/2008 | Reiley |
| 2008/0269761 A1 | 10/2008 | Truckai |
| 2008/0269795 A1 | 10/2008 | Reiley et al. |
| 2008/0269796 A1 | 10/2008 | Reiley et al. |
| 2008/0281346 A1 | 11/2008 | Greenhalgh |

(56) References Cited

U.S. PATENT DOCUMENTS

| | | |
|---|---|---|
| 2008/0281364 A1 | 11/2008 | Chirico et al. |
| 2008/0294166 A1 | 11/2008 | Goldin |
| 2008/0294205 A1 | 11/2008 | Greenhalgh |
| 2008/0300604 A1 | 12/2008 | Lu |
| 2009/0005790 A1 | 1/2009 | Pacheco |
| 2009/0018524 A1 | 1/2009 | Greenhalgh |
| 2009/0030468 A1 | 1/2009 | Sennett |
| 2009/0054934 A1 | 2/2009 | Beyar |
| 2009/0069850 A1 | 3/2009 | Fuerderer |
| 2009/0076517 A1 | 3/2009 | Reiley et al. |
| 2009/0076607 A1 | 3/2009 | Aalsma |
| 2009/0088788 A1 | 4/2009 | Mouw |
| 2009/0101157 A1 | 4/2009 | Karmon |
| 2009/0112207 A1 | 4/2009 | Walker |
| 2009/0112262 A1 | 4/2009 | Pool |
| 2009/0112263 A1 | 4/2009 | Pool |
| 2009/0125031 A1 | 5/2009 | Melsheimer et al. |
| 2009/0131952 A1 | 5/2009 | Schumacher |
| 2009/0138043 A1 | 5/2009 | Kohm |
| 2009/0157084 A1 | 6/2009 | Aalsma |
| 2009/0157087 A1 | 6/2009 | Wei et al. |
| 2009/0163918 A1 | 6/2009 | Levy |
| 2009/0164016 A1 | 6/2009 | Georgy |
| 2009/0171361 A1 | 7/2009 | Melsheimer et al. |
| 2009/0171362 A1 | 7/2009 | Schaeffer |
| 2009/0171393 A9 | 7/2009 | Johnson |
| 2009/0177153 A1 | 7/2009 | Saab |
| 2009/0177200 A1 | 7/2009 | Saab |
| 2009/0177206 A1 | 7/2009 | Lozier |
| 2009/0177207 A1 | 7/2009 | Schaller |
| 2009/0177235 A1 | 7/2009 | Saab |
| 2009/0177236 A1 | 7/2009 | Saab |
| 2009/0182339 A1 | 7/2009 | Johnson |
| 2009/0182386 A1 | 7/2009 | Schaller |
| 2009/0187190 A1 | 7/2009 | Johnson |
| 2009/0187192 A1 | 7/2009 | Rabiner |
| 2009/0187249 A1 | 7/2009 | Osman |
| 2009/0299401 A1* | 12/2009 | Tilson ............... 606/192 |
| 2010/0076480 A1 | 3/2010 | Lu |
| 2011/0137317 A1 | 6/2011 | O'halloran |
| 2012/0010624 A1 | 1/2012 | O'halloran |
| 2012/0010713 A1 | 1/2012 | O'halloran |
| 2012/0016369 A1 | 1/2012 | O'halloran |
| 2012/0016371 A1 | 1/2012 | O'halloran |

OTHER PUBLICATIONS

U.S. Appl. No. 08/485,394 Mark A Reiley filed Jun. 7, 1995 Inflatable Device for Use in Surgical Protocols Relating to Treatment of Fractured or Diseased Bone.

U.S. Appl. No. 08/986,876 Mark A Reiley filed Dec. 8, 1997 Systems and Methods Using Expandable Bodies to Push Apart Cortical Bone Surfaces.

U.S. Appl. No. 08/799,832 Mark A. Reiley filed Feb. 13, 1997 Inflatable Device for Use in Surgical Protocol Relating to Treatment of Fracture of Diseases Bone.

U.S. Appl. No. 10/054,736 Paul Reiss filed Jun. 8, 2004 Devices and Methods Using an Expandable Body With Internal Restraint for Compressing Cancellous Bone.

U.S. Appl. No. 09/088,459 Robert Scribner filed Jun. 1, 1998 Expandable Preformed Structures for Deployment in Interior Body Regions.

U.S. Appl. No. 12/171,168 Guobao Wei, filed Jul. 10, 2008 Delivery System.

U.S. Appl. No. 11/263,675 James R. Johnson filed Oct. 31, 2005 Packable Ceramic Beads for Bone Repair.

U.S. Appl. No. 12/419,076 James R. Johnson filed Apr. 6, 2009 Packable Ceramic Beads for Bone Repair.

* cited by examiner

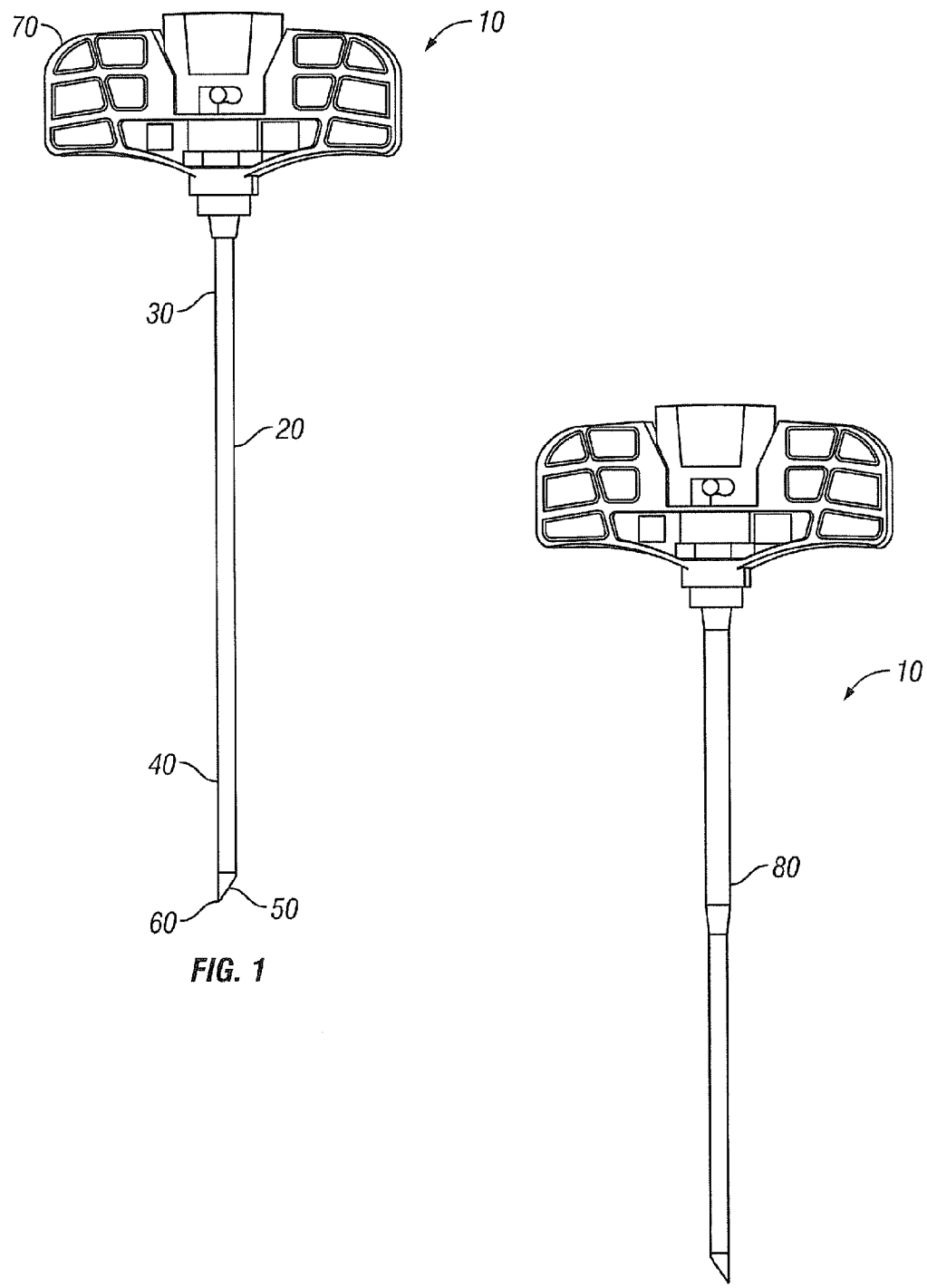

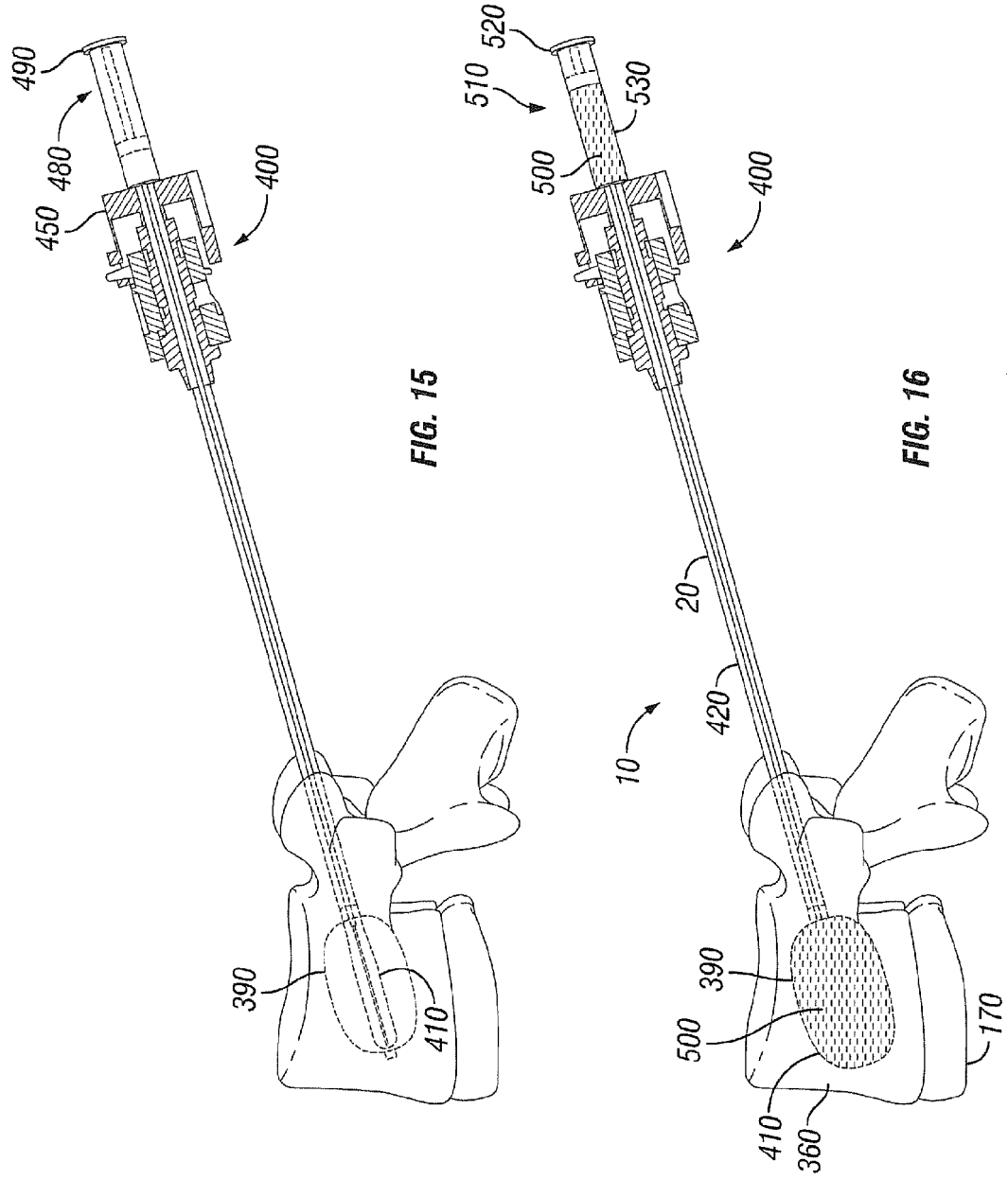

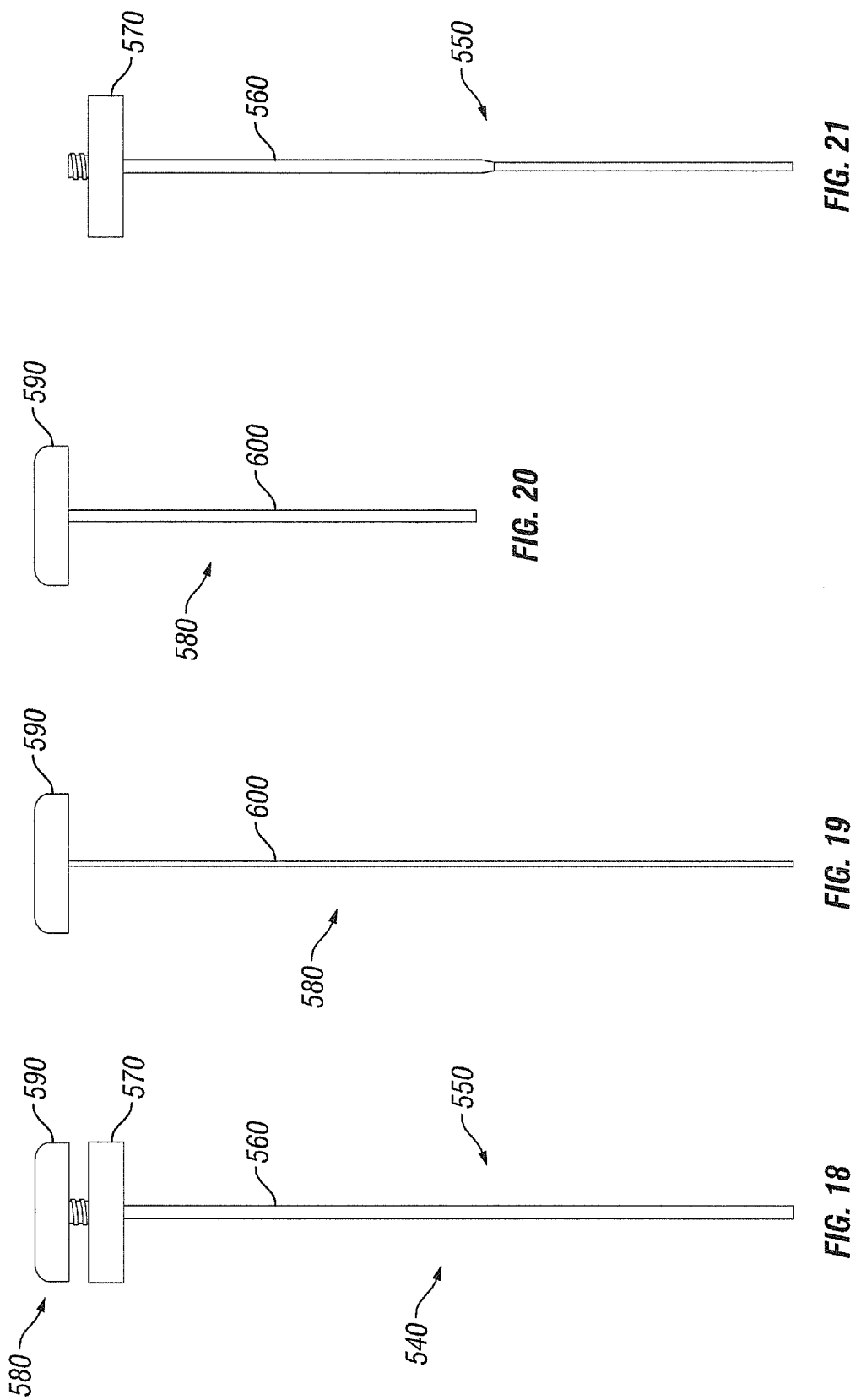

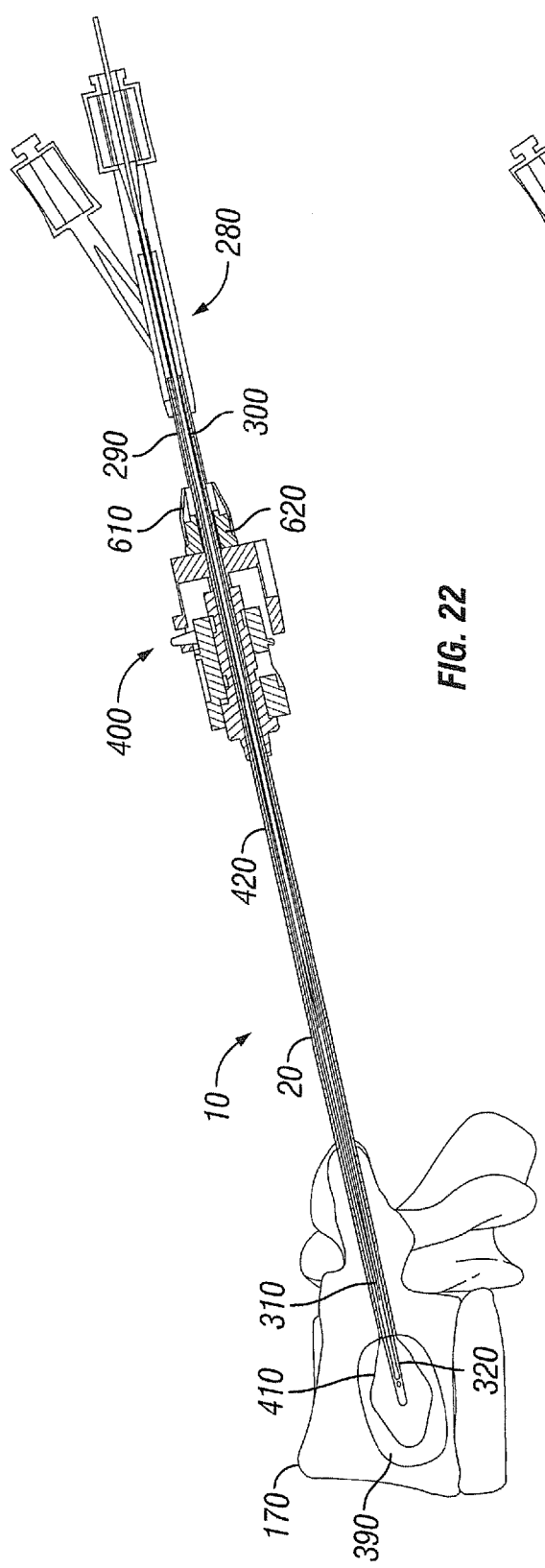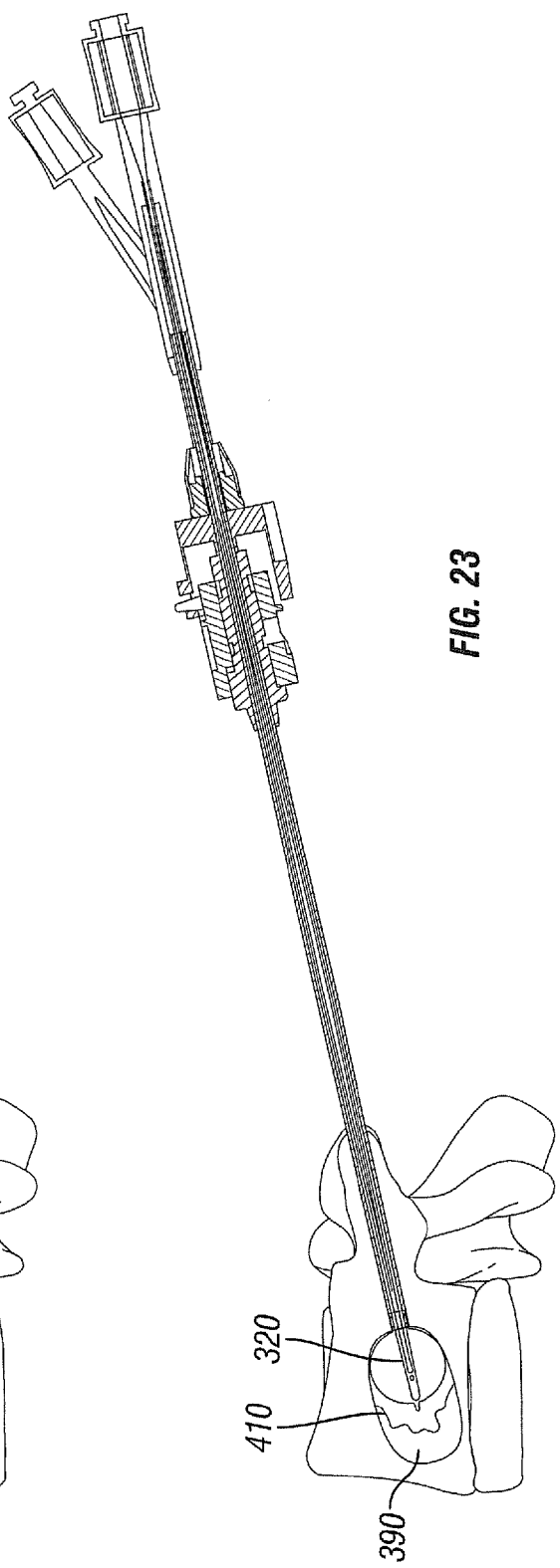
FIG. 22
FIG. 23

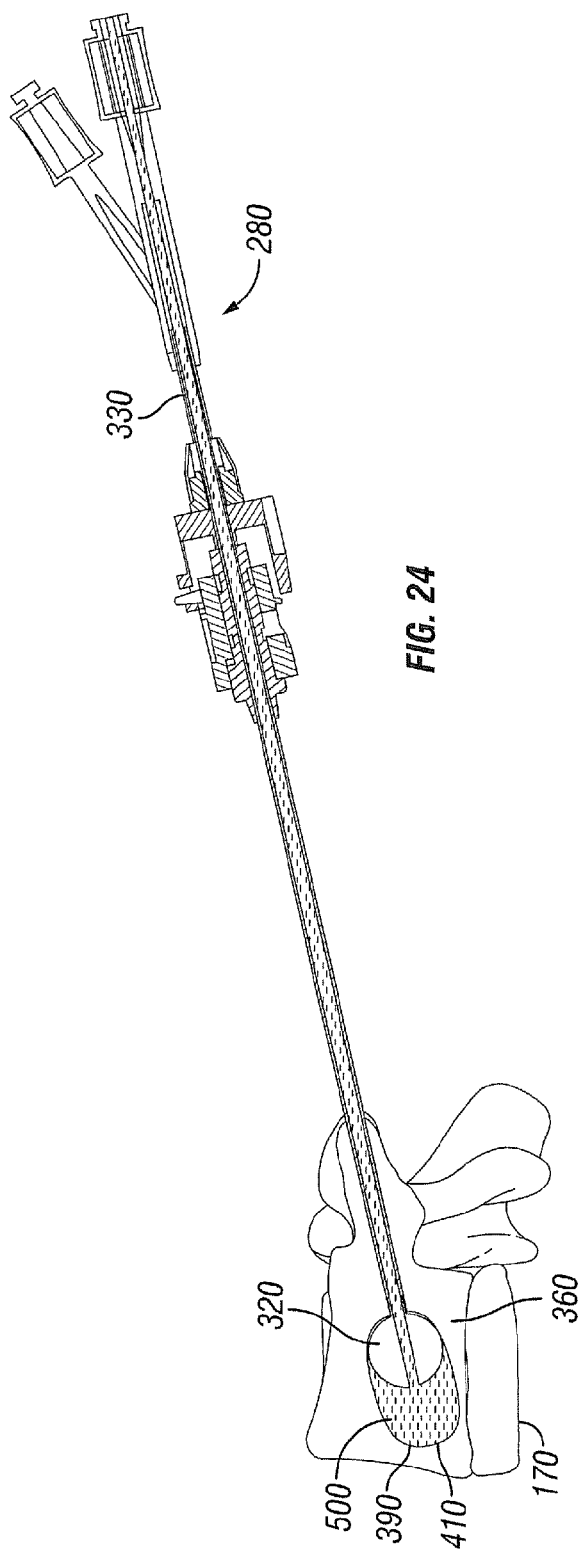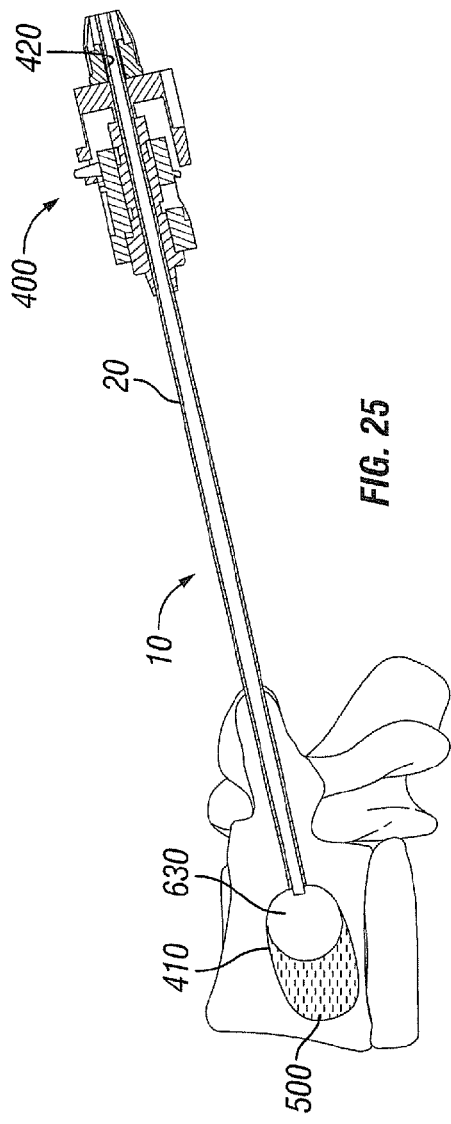

METHODS AND APPARATUS FOR TREATING VERTEBRAL FRACTURES

FIELD OF THE INVENTION

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

BACKGROUND

Bones and bony structures are susceptible to a variety of weaknesses that can affect their ability to provide support and structure. Weaknesses in bony structures may have many causes, including degenerative diseases, tumors, fractures, and dislocations. By way of example, weaknesses in vertebrae can lead to compression fractures that involve the collapse of one or more vertebrae in the spine. These vertebral compression fractures may be caused by a number of conditions including osteoporosis, trauma, and tumors. Advances in medicine and engineering have provided doctors with a plurality of devices and techniques for alleviating or curing these weaknesses.

One technique for treating vertebral fractures is vertebroplasty. In vertebroplasty, a physician may use a needle to inject bone cement into a fractured vertebral body to stabilize the fracture. Kyphoplasty is another technique for treating vertebra fractures that involves insertion of a balloon into the fractured vertebra to restore the height of the vertebra. The balloon may then be removed followed by injection of bone cement into the vertebral body to stabilize the fracture. Leakage of the bone cement in both vertebroplasty and kyphoplasty is a common problem that can lead to complications. Another problem associated with these techniques is the potential for inadequate height restoration to the fractured vertebral body.

Thus, there is a need for methods and apparatus that can provide stabilization to a fractured vertebra.

SUMMARY

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

An embodiment includes a method for treating a bone. The method may comprise inserting a cannula having an inner lumen into the bone. The method may further comprise creating a cavity in the bone. The method may further comprise providing a containment assembly. The containment assembly may comprise a tubular member having a proximal end and a distal end. The containment assembly may further comprise a containment jacket disposed on the distal end of the tubular member. The containment assembly may further comprise a guide wire disposed through the tubular member with the guide extending into the containment jacket. The method may further comprise inserting the containment jacket through the inner lumen of the cannula and into the cavity. The method may further comprise introducing a filler material into the containment jacket.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

FIG. 1 illustrates a cannula assembly in accordance with one embodiment of the present technique.

FIG. 2 illustrates a cannula assembly having a tapered cannula in accordance with one embodiment of the present invention.

FIG. 15 illustrates removal of fluid from a containment jacket placed in a vertebral body in accordance with one embodiment of the present invention.

FIG. 16 illustrates use of a syringe-type device to introduce filler material into a containment jacket placed in a vertebral body in accordance with one embodiment of the present invention.

FIGS. 18-21 illustrate needle-type devices that may be used in accordance with embodiments of the present invention.

FIG. 22 illustrates insertion of a balloon into a containment jacket placed in a vertebral body in accordance with one embodiment of the present invention.

FIG. 23 illustrates inflation of a balloon in a containment jacket placed within a vertebral body in accordance with one embodiment of the present invention.

FIG. 24 illustrates introduction of a filler material into a vertebral body while using a balloon in accordance with one embodiment of the present invention.

FIG. 25 illustrates a containment jacket placed within a vertebral body that has been partially filled in accordance with one embodiment of the present invention.

DETAILED DESCRIPTION OF THE ILLUSTRATED EMBODIMENTS

Figures 3, 4:
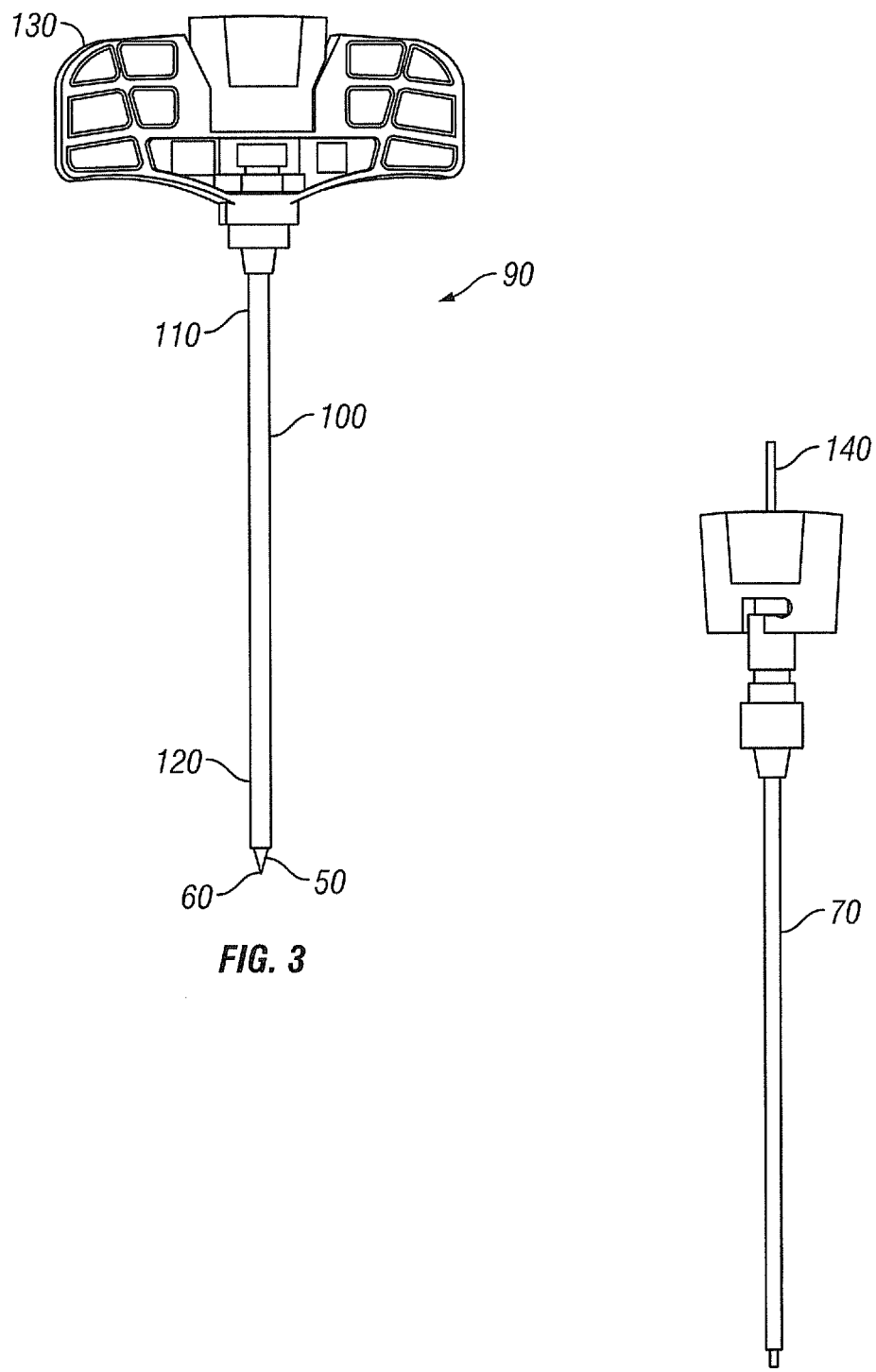
FIG. 3 illustrates a needle assembly in accordance with one embodiment of the present invention.
FIG. 4 illustrates a needle assembly having a guide wire disposed therethrough in accordance with one embodiment of the present invention.

Embodiments of the present technique for treating vertebral fractures may include creating an access channel into a vertebral body. FIG. 1 illustrates a cannula assembly 10 that may be used to create an access channel through a patient's tissue to a vertebral body (not illustrated) in accordance with one embodiment of the present invention. In the illustrated embodiment, the cannula assembly 10 comprises a cannula 20 configured to allow passage of various instruments and materials into the vertebral body. The cannula 20 may have a proximal end 30 and a distal end 40. The cannula assembly 10 further may include a stylet 50 removably disposed in the cannula 20. As illustrated, the stylet 50 may have a pointed end 60 that extends beyond the distal end 40 of the cannula 20. In an embodiment, the cannula assembly 10 may further comprise a handle 70 disposed on the proximal end of the cannula 20. In an embodiment, the cannula assembly 10 may be a trocar-tipped cannula. By way of example, the cannula assembly 10 may be a diamond, scoop, bevel, trocar tipped cannula.

To create the access channel, the physician may make an incision in the patient's back, for example. The distal end 40 of the cannula 20 may be inserted into the incision. The physician may then apply longitudinal force to the cannula assembly 10 while rotating the handle 70 to advance the cannula 20 through the patient's tissue and into a vertebral body. In other embodiments, the handle 70 may use other mechanisms to advance the cannula 20 through the patient's tissue, such as a ratcheting system. In an embodiment, the cannula 20 may be inserted into the vertebral body through a pedicle. Once the cannula 20 has been inserted into the vertebral body, the stylet 50 and handle 70 may be removed, leaving the cannula 20. In this manner, the cannula 20 may provide an access channel into the vertebral body.

While the cannula assembly 10 may be suited for creating an access channel to vertebral bodies in all regions of the vertebral column, the cannula assembly 10 may be particularly suited for access in the middle of the thoracic region and lower. If access is desired from the middle of the thoracic region and above, a device having a tapered cannula may be used, in accordance with one embodiment. FIG. 2 illustrates a cannula assembly 10 having a tapered cannula 80 in accordance with an embodiment of the present invention. While the tapered cannula 80 may be particularly suited for accessing the middle of the thoracic region and above, it should be understood that the tapered cannula 80 may also be used to create an access channel to vertebral bodies in all regions of the vertebral column.

While FIG. 1-2 describe use of a cannula assembly 10 that is sharp and pointed for creating an access channel into a vertebral body, it should be understood that a variety of different devices and techniques may be used to create the access channel in accordance with embodiment of the present invention. Referring now to FIGS. 3-6, an alternative technique for creating an access channel into a vertebral body is illustrated in accordance with one embodiment of the present invention.

FIG. 3 illustrates a needle assembly 90 that may be used to create an access channel through a patient's tissue to a vertebral body (not illustrated) in accordance with an embodiment of the present invention. In the illustrated embodiment, the needle assembly 90 comprises a needle 100 having a proximal end 110 and a distal end 120. The needle assembly 90 further may include a stylet 50 removably disposed in the needle 100. As illustrated, the stylet 50 may have a pointed end 60 that extends beyond the distal end 120 of the needle 100. As illustrated, the needle assembly 90 may further comprise a handle 130 disposed on the proximal end 110 of the needle 100. In an embodiment, the needle assembly 90 is a diamond, bevel tipped Jamshidi needle.

The needle assembly 90 of FIG. 3 may be inserted into the vertebral body in a similar manner to the cannula assembly 10 of FIG. 1. By way of example, the distal end 120 of the needle 100 may be inserted into an incision in the patient's back. To advance the needle 100 into the vertebral body, longitudinal force may then be applied to the needle assembly 90 while rotating the handle 130. The stylet 50 and handle 130 may then be removed, leaving the needle 100. As illustrated by FIG. 4, a guide wire 140 (e.g., a k-wire) may be disposed through the needle 100 and into the vertebral body. With the guide wire 140 in place, the needle 100 may be removed.

Figures 5, 6:
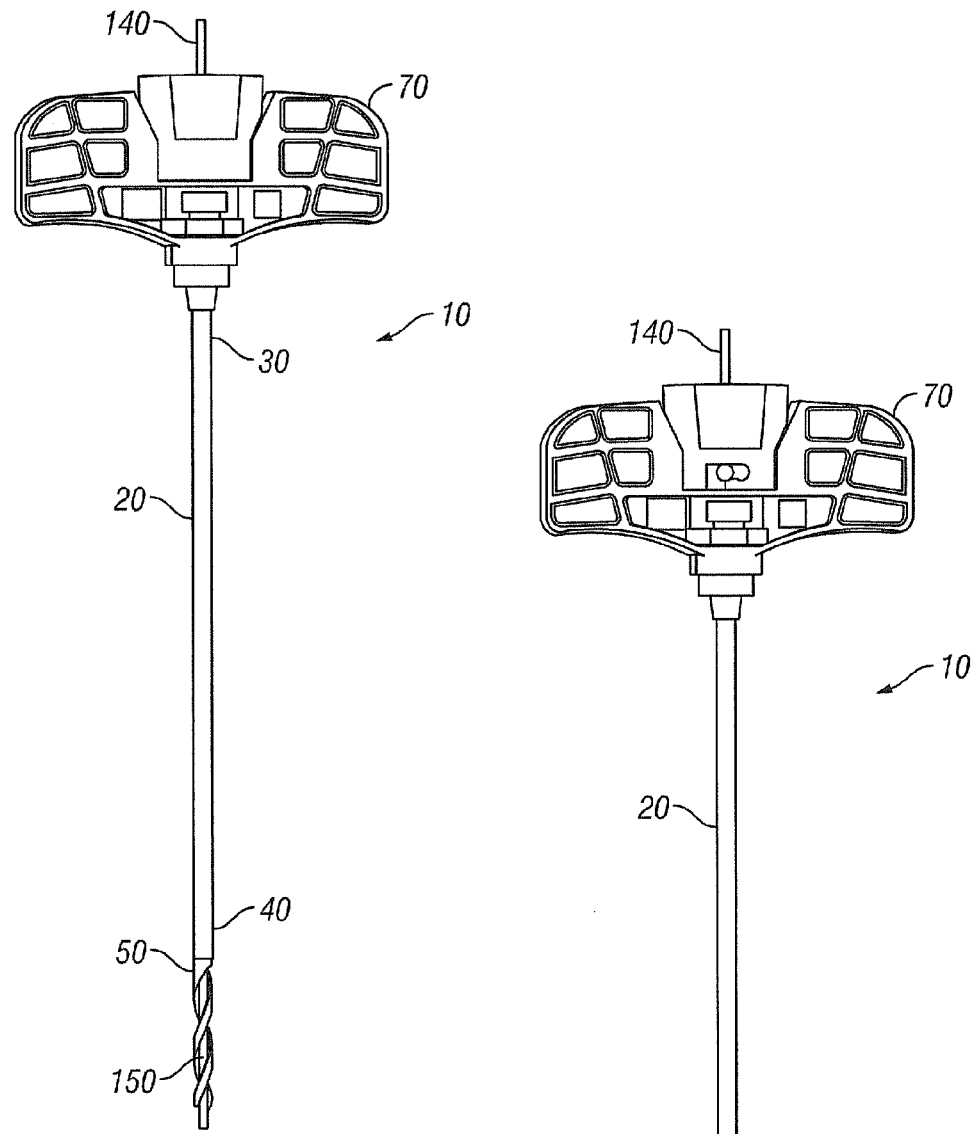
FIG. 5 illustrates a cannula assembly disposed over a guide wire and having a drill-tip stylet in accordance with one embodiment of the present invention.
FIG. 6 illustrates a cannula assembly disposed over a guide wire and having a conical-tip stylet in accordance with one embodiment of the present invention.

As illustrated by FIG. 5, after removal of the needle 100, a cannula assembly 10 may be inserted over the guide wire 140 and into the vertebral body. In the illustrated embodiment, the cannula assembly 10 includes a cannula 20 having a handle 70 disposed on the proximal end 30. In an embodiment, a stylet 50 having a drill-shaped end 150 may be disposed in the cannula 20. As illustrated, the drill-shaped end 150 of the stylet 50 may extend out from the distal end 40 of the cannula 20. FIG. 6 illustrates an alternative embodiment of the cannula assembly 10. As illustrated by FIG. 6, the stylet 50 disposed in the cannula 20 may have a conically shaped end 160 extending out from the distal end 40 of the cannula 20. To advance the cannula assembly 10 over the guide wire 140 and through the patient's tissue, the physician may apply longitudinal force to the cannula assembly 10 while rotating the handle 70. Once the cannula assembly 10 has been inserted into the vertebral body, the stylet 50, handle 70, and guide wire 140 may be removed, leaving the cannula 20. In this manner, the cannula 20 may provide an access channel into the vertebral body.

Figure 7:
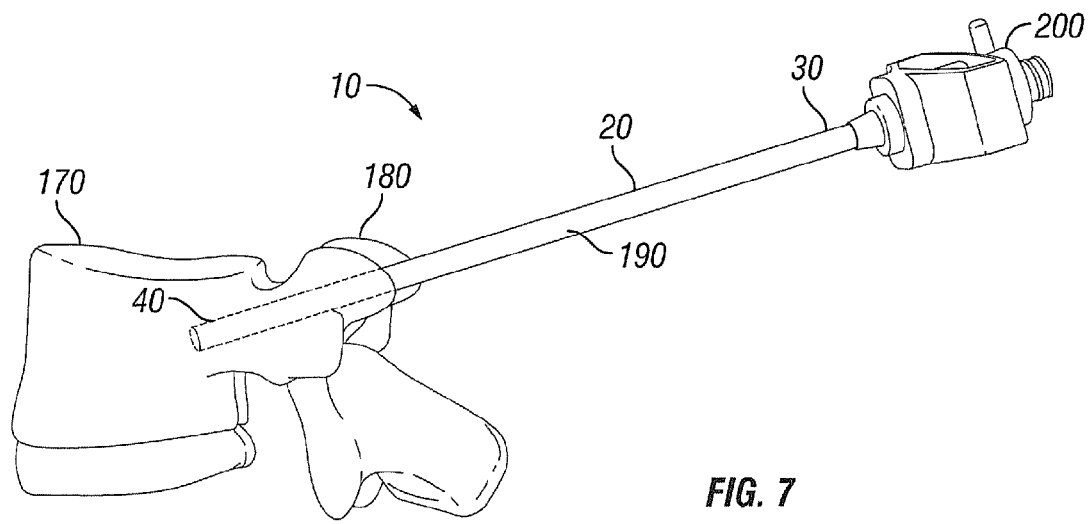
FIG. 7 illustrates a cannula assembly inserted into a vertebral body in accordance with one embodiment of the present invention.

FIG. 7 illustrates a cannula assembly 10 that has been inserted into a vertebral body 170 to provide access to the vertebral body 170 in accordance with one embodiment of the present invention. In an embodiment, the cannula assembly 10 may be inserted into the vertebral body 170 through a pedicle 180. In an embodiment (not illustrated), the cannula assembly 10 is not inserted through the pedicle 180. In the illustrated embodiment, the cannula assembly 10 includes a cannula 20 having a proximal end 30 and a distal end 40 extending into the vertebral body 170. As illustrated, cannula 20 may include an inner lumen 190 configured to allow passage of various instruments and materials into the vertebral body 170. The cannula assembly 10 further may include a cannula hub 200 disposed on the proximal end 30 of the cannula 20.

Figure 8:
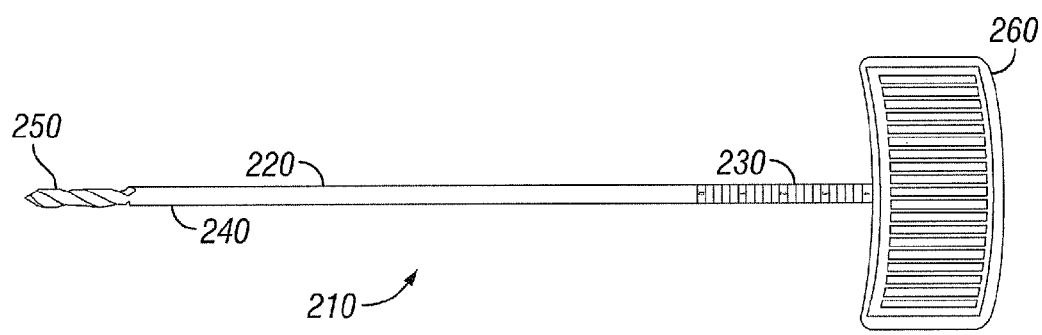
FIG. 8 illustrates a drill that can be used in accordance with one embodiment of the present invention.
Figure 9:
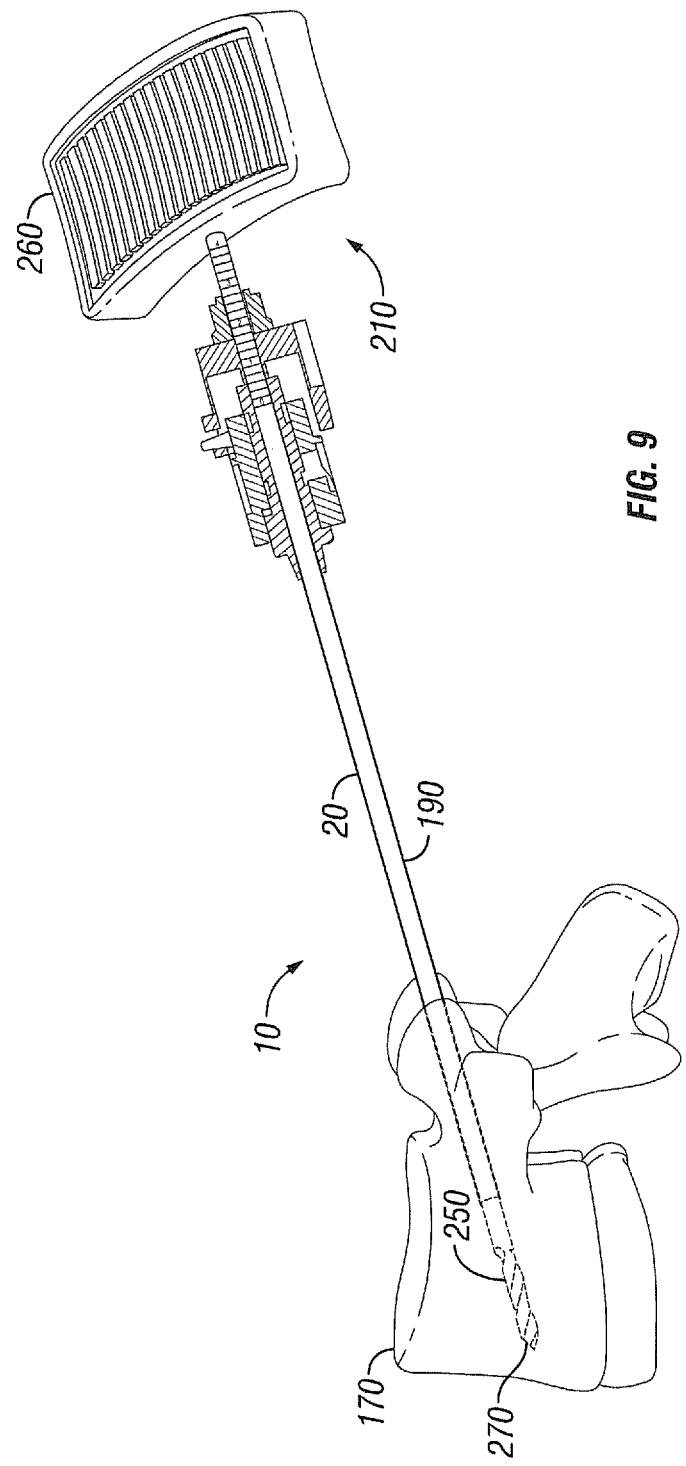
FIG. 9 illustrates insertion of a drill through the cannula assembly to create a channel in a vertebral body in accordance with one embodiment of the present invention.

Embodiments of the present technique for treating vertebral fractures may further include creating a channel in the vertebral body 170. FIG. 8 illustrates a drill 210 that may be used to create the channel in the vertebral body 170 in accordance with one embodiment of the present invention. In the illustrated embodiment, the drill 210 comprises a shaft 220 having a proximal end 230 and a distal end 240. A bit 250 may extend from the distal end 240 of the shaft 220. A handle 260 may be disposed on the proximal end 230 of the shaft. As illustrated by FIG. 9, the drill 210 may be used to create a channel 270 in the vertebral body 170. By way of example, the physician may insert the drill 210 through the inner lumen 190 of the cannula 20 until the bit 250 contacts bone (e.g., cancellous bone) within the vertebral body 170. The channel 270 in the vertebral body 170 may then be created by application of longitudinal forces to the drill 210 while rotating the handle 260. The drill 210 may then be removed from the cannula 20 leaving the cannula assembly 10 in place, for example, with the cannula 20 providing access to the channel 270 within the vertebral body 170.

Figure 10:
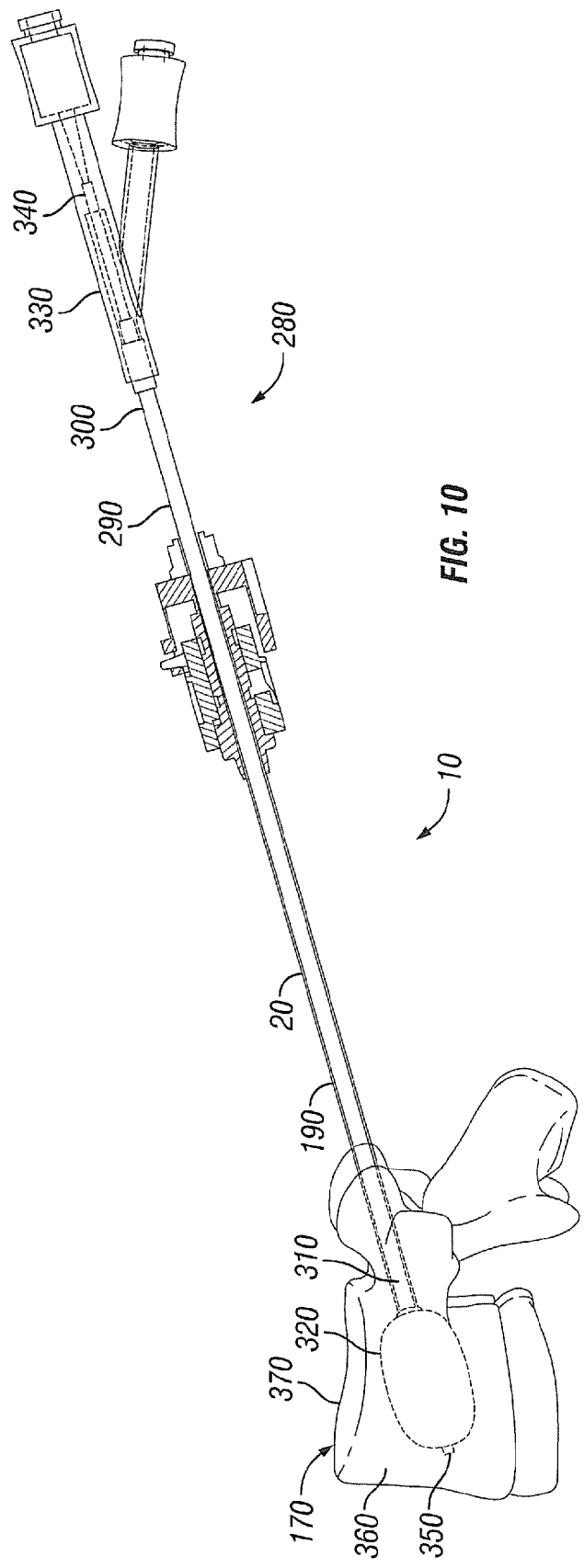
FIG. 10 illustrates insertion of a balloon into a vertebral body in accordance with one embodiment of the present invention.

Embodiments of the present technique for treating vertebral fractures may further include creating a cavity in a vertebral body 170. FIG. 10 illustrates creation of a cavity in vertebral body 170 with a balloon assembly 280 in accordance with one embodiment of the present invention. As illustrated, cannula assembly 10 has been inserted into the vertebral body 170 with the cannula 20 providing access into the vertebral body 170. To create the cavity, balloon assembly 280 may be inserted into the previously created channel 270 (illustrated on FIG. 9) in the vertebral body 170 through the inner lumen 190 of the cannula 20. In certain embodiments, the balloon assembly 280 may be an inflatable bone tamp. In the illustrated embodiment, the balloon assembly 280 includes a catheter 290 having a proximal end 300 and a distal end 310. A balloon 320 may be attached to the distal end 310 of the catheter 290. While FIG. 10 illustrates the balloon 320 in an expanded configuration, it should be understood that the balloon 320 should be inserted into the vertebral body 170 in a deflated state. The balloon 320 used to create the cavity may include any of a variety of different balloons suitable for use in medical procedures. Examples of suitable balloons include those commonly used in kyphoplasty, including those comprising plastics, composite materials, polyethylene, mylar, rubber, polyurethane, or any other suitable material. As illustrated, the balloon assembly 280 may further include an inner lumen 340 disposed within the catheter 290. As illustrated, the inner catheter 330 has an inner lumen 340 with an exit port 350, for example, that extends beyond the balloon 320.

As illustrated by FIG. 10, the balloon 320 may be inflated, for example, to compact the cancellous bone 360 in the interior portion of the vertebral body 170 enlarging the channel (illustrated on FIG. 9) to create a cavity within the vertebral body 170. In addition to creation of the cavity, the balloon 320 may also, for example, force apart the compact bone 370, restoring height to the vertebral body 170. After cavity creation, the balloon 320 may be deflated and removed from the vertebral body 170.

Figure 11:
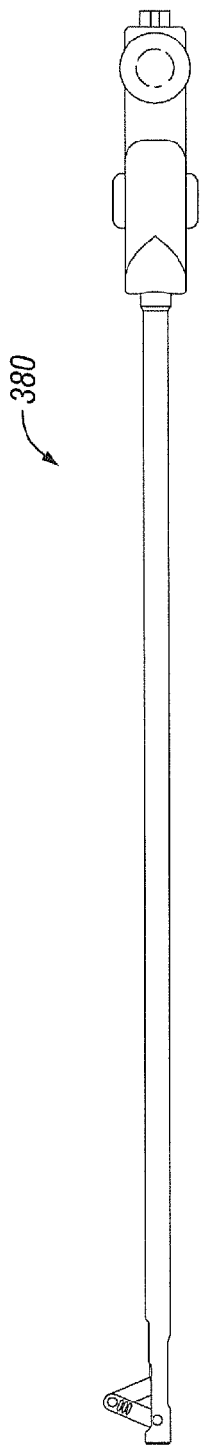
FIG. 11 illustrates a mechanical device that can be used to create a cavity in a vertebral body in accordance with one embodiment of the present invention.

While FIG. 10 illustrates the use of the balloon assembly 280 for creation of the cavity in the vertebral body 170, those of ordinary skill in the art will appreciate that other suitable techniques may also be used for creation of the cavity. By way of example, an expandable jack or other suitable mechanical device may be used to create the cavity in the vertebral body 170. FIG. 11 illustrates a mechanical device 380 that may be used to create the cavity in accordance with one embodiment of the present invention. In an embodiment, the mechanical device 380 may be inserted through the cannula assembly 10 and into the vertebral body 170. The mechanical device 380 may then be activated to create the cavity.

Figure 12:
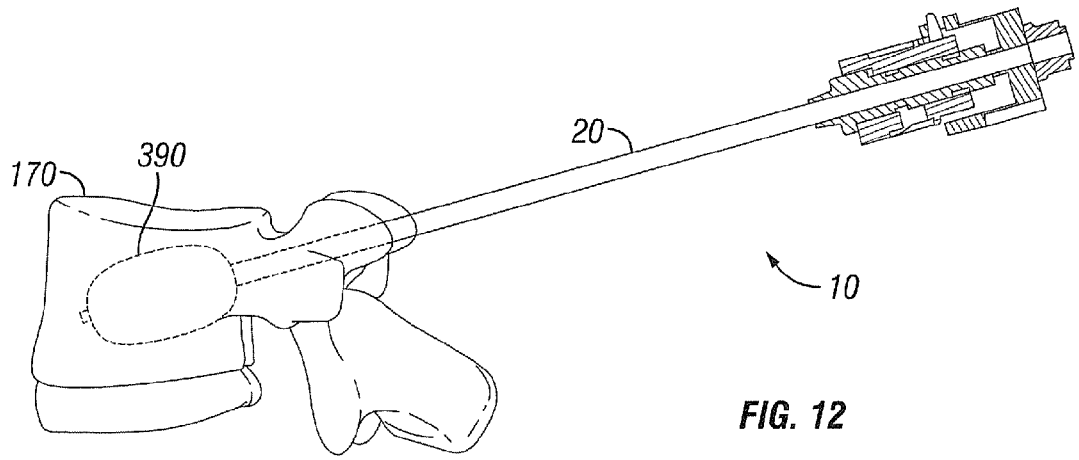
FIG. 12 illustrates a cavity in a vertebral body in accordance with one embodiment of the present invention.

FIG. 12 illustrates a cavity 390 that has been created in the vertebral body 170 in accordance with one embodiment of the present invention. In accordance with present embodiments, the cavity 390 may be formed using an inflatable balloon, a mechanical device, or a combination of both. As illustrated, the cannula 20 of the cannula assembly 10 should extend into the cavity 390, providing access to the cavity 390. While not illustrated, embodiments of the present invention further may include coating the wall of the cavity 390 with a bone growing agent.

In accordance with embodiments of the present invention, a filler material may be introduced into the cavity 390, for example, to stabilize a fracture in the vertebral body 170. However, prior to insertion of the filler material, embodiments of the present technique further may include inserting a containment jacket into the cavity 390 in the vertebral body 170. The containment jacket may be employed to contain the filler material (e.g., cement) introduced into the cavity 390, for example, to prevent undesirable leakage. In this manner, problems associated with leakage of the filler material from the cavity 390.

Figure 13:
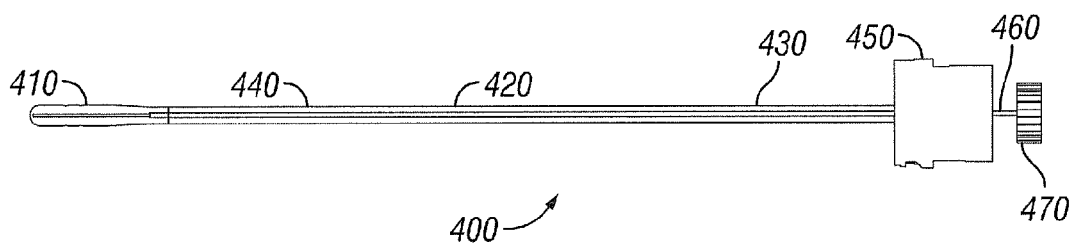
FIG. 13 illustrates a containment assembly in accordance with one embodiment of the present invention.

FIG. 13 illustrates a containment assembly 400 having a containment jacket 410 that may be inserted into the cavity. As illustrated, the containment assembly 400 comprises a tubular member 420 (e.g., a cannula) having a proximal end 430 and a distal end 440. The tubular member 420 may be configured to allow passage of various instruments and materials into a vertebral body. The containment jacket 410 may be disposed on the distal end 440 of the tubular member 420. In an embodiment, the containment jacket 410 is impermeable, e.g., to the filler material. As illustrated, a hub 450 may be disposed on the proximal end 430 of the tubular member 420. The hub 450 may allow connection of the containment assembly 400 to other devices that may be used in a medical procedure. A guide wire 460 (e.g., a K-wire) may be disposed through the tubular member 430. As illustrated, the guide wire 460 may extend into the proximal end 430 of the tubular member 420 and out from the distal end 440 of the tubular member 420. In an embodiment, the containment jacket 410 is disposed on the portion of the guide wire 460 extending from the distal end 440 of the tubular member 420. For example, the containment jacket 410 may be wrapped around the portion of the guide wire 460 extending through the distal end 440 of the tubular member 420. In this manner, the guide wire 460 may facilitate insertion of the containment jacket 410 through the cannula 20. In the illustrated embodiment, a cap 470 is disposed on the end of the guide wire 460 extending from the proximal end 430 of the tubular member 420.

Figure 14:
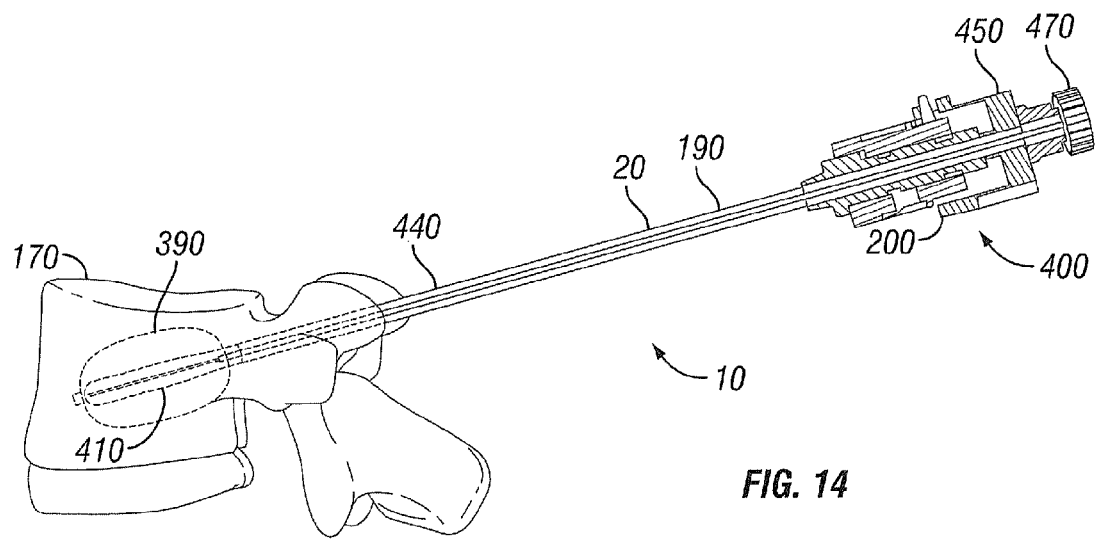
FIG. 14 illustrates insertion of a containment assembly into a vertebral body in accordance with one embodiment of the present invention.

As illustrated by FIG. 14, the containment jacket 410 may be inserted through the inner lumen 190 of the cannula 20 and into the cavity 390 within the vertebral body 170. In an embodiment, the containment jacket 410 may be in an unfolded state when it is inserted into the cavity 390. The containment jacket 410 may be inserted by sliding the tubular member 440 with the containment jacket 410 disposed thereon through the cannula 20 of the cannula assembly 10. In an embodiment, the hub 450 on the containment assembly 400 may be coupled to the cannula hub 200 on the cannula assembly 10. Once the containment jacket 410 has been placed, the guide wire 460 (shown on FIG. 13) may be removed from the containment assembly 400, leaving the containment jacket 410 in place. The cap 470 may be used to facilitate removal of the guide wire 460.

Embodiments of the present technique for treating vertebral fractures may further include removing fluid (e.g., air) from within the containment jacket 410 that has been placed into the vertebral body 170. Any of a variety of different techniques may be used to remove air from within the containment jacket. In an embodiment, a syringe may be used remove the air. An example of a suitable syringe includes a VacLok™ syringe. As illustrated by FIG. 15, a syringe 480 may be coupled to the hub 450 of the containment assembly 400. The plunger 490 of the syringe 480 may then be withdrawn to create a partial vacuum so that air from within the containment jacket 410 flows into the syringe 480. Accordingly, the fluid in the containment jacket 410 may be removed.

Figure 17:
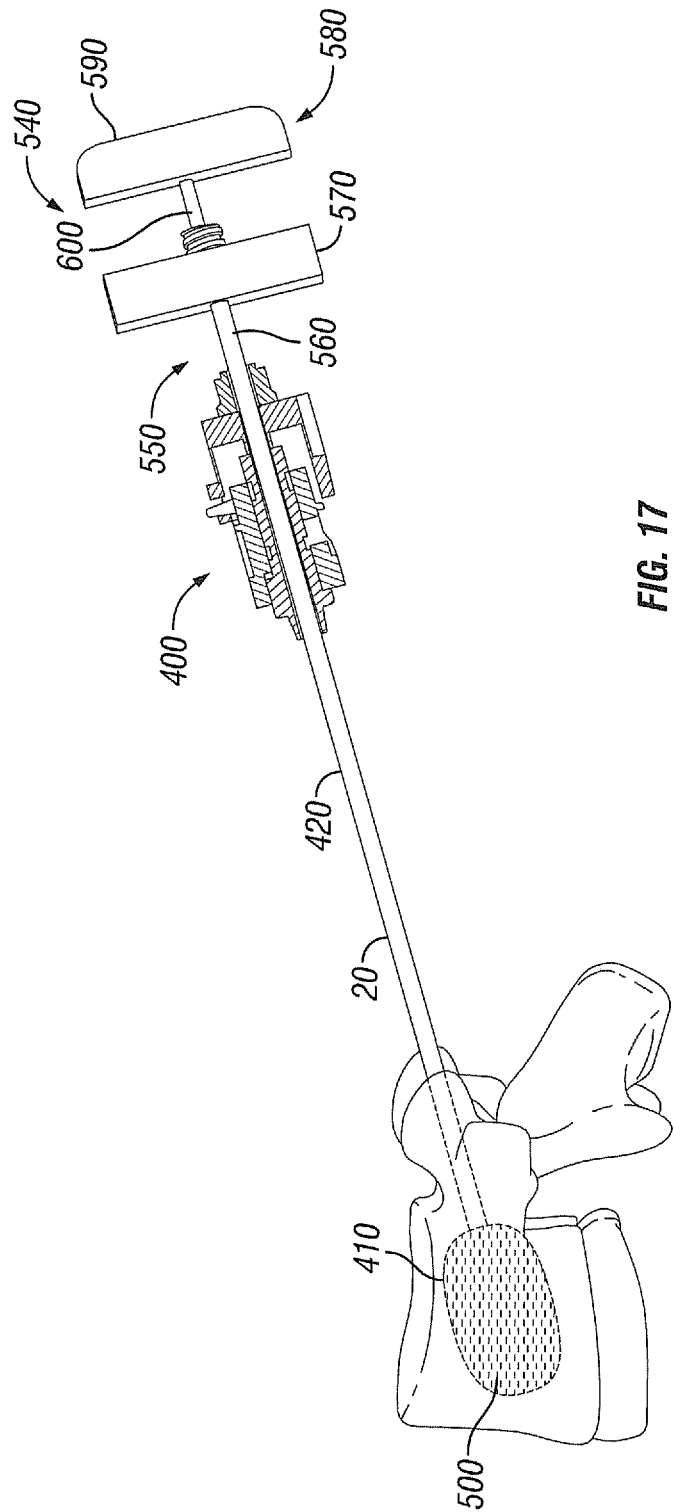
FIG. 17 illustrates use of a needle-type device to introduce filler material into a containment jacket placed in a vertebral body in accordance with one embodiment of the present invention.

As previously mentioned, embodiments of the present invention may further include introduction of a filler material into the cavity 390. In an embodiment, the filler material may be introduced directly into the containment jacket 410 that has been placed within the cavity 390. FIGS. 16 and 17 illustrate a procedure comprising introduction of a filler material 500 into the containment jacket 410 in accordance with one embodiment of the present invention. In an alternative embodiment, a balloon assembly 280 may be used while introducing the filler material into the containment jacket 410. FIGS. 22-27 illustrate use of the balloon assembly 280 with the containment jacket 410 in accordance with one embodiment of the present invention.

FIG. 16 illustrates introduction of filler material 500 into the containment jacket 410 using a syringe-type device 510. As illustrated, plunger 520 of the syringe-type device 510 may be depressed to force filler material 500 from the body 530 of the syringe-type device 510, through the tubular member 420 of the containment assembly, and into the containment jacket 410. In an embodiment, introduction of the filler material 500 into the containment jacket 410 should expand the containment jacket 410. In some embodiments, the filler material 500 may be introduced into the containment jacket 410 until the containment jacket 410 at least partially fills the cavity 390 in the vertebral body 170. In general, the filler material 500 should exert pressure to prevent (or reduce) loss of vertebral height. It may be desirable, in certain embodiments, for the filler material 500 to exert pressure that further increases height of the vertebral body 170. In certain embodiments, the filler material 500 may exert pressure that restores some height lost after removal of the balloon 320. As illustrated, the containment jacket 410 may generally conform to the shape of the cavity 390. It may be desirable, in certain embodiments, for the containment jacket 410 to be a complaint balloon (e.g., polyurethane, collagen, silicone) that can contain the filler material 500 to prevent leakage. The containment jacket 410 may permit interdigitation of the filler material 500 with the cancellous bone 360 while being contained within the containment jacket 410.

While FIG. 16 illustrates use of syringe-type device 510 for introduction of the filler material 500, it should be understood that other suitable devices may be used to introduce the filler material 500 into the vertebral body 170. For example, FIGS. 17-21 illustrate a needle-type device 540 that may be used to introduce the filler material 500. As illustrated, the body 550 of the needle-type device 540 comprises a hollow tube 560 having a through passageway and a stop 570 at one end. The needle-type device 540 further comprises a plunger 580 having a depression mechanism 590 and a needle 600 for insertion into the hollow tube 560. The length of the needle 600 may vary. For example, FIGS. 19 and 20 illustrate needles 600 that vary in length with the needle 600 of FIG. 19 longer in length. In an embodiment, the body 550 of the needle-type device 540 may be inserted into the tubular member 420 of the containment assembly 400. Plunger 580 may then be depressed to force the filler material 500 from the body 560 of the needle-type device 540 and into the containment jacket 410.

In addition to introducing the filler material 500 directly into the containment jacket 410 as illustrated by FIGS. 15 and 16, alternative embodiments of the present invention may utilize a balloon assembly 280 while introducing the filler material 500 into the containment jacket 410. The balloon assembly 280 may be used, for example, to maintain and/or restore vertebral height while introducing the filler material 500. FIGS. 22-27 and the accompanying description illustrate use of the balloon assembly 280 with the containment jacket 410 in accordance with one embodiment of the present invention.

FIG. 22 illustrates insertion of balloon assembly 280 into the vertebral body 170 through the containment assembly 400 and the cannula assembly 10 in accordance with one embodiment of the present invention. As illustrated, cannula assembly 10 has been inserted into the vertebral body 170 with the cannula 20 providing access into the vertebral body 170. As further illustrated, the containment jacket 410 has already been inserted into the cavity 390. In an embodiment, the containment jacket 410 may be inserted by sliding the tubular member 440 with the containment jacket 410 disposed thereon through the cannula 20 of the cannula assembly 10. In accordance with embodiments of the present invention, the balloon assembly 280 may be inserted into vertebral body 170. As illustrated, the balloon assembly 280 includes a catheter 290 having a proximal end 300 and a distal end 310. A balloon 320 may be attached to the distal end 310 of the catheter 290.

As illustrated by FIG. 22, the balloon 320 may be inserted may be inserted into the containment jacket 410 through the tubular member 420 of the containment assembly 400. In an embodiment, the balloon 320 may be in a deflated stated when inserted through the tubular member 420. The balloon 320 may be inserted by sliding the catheter 290 with the balloon 320 disposed on the distal end 310 thereof through the tubular member 420 of the containment assembly 400. Once the balloon 320 has been placed, the balloon assembly 280 may be coupled to the containment assembly 400. By way of example, cap 610 disposed on the catheter 290 of the balloon assembly 280 may thread onto a luer fitting 620 on the hub 450 of the containment assembly 400. After insertion of the balloon 320, fluid (e.g., air) may be removed from the containment jacket 410. The fluid may be removed, for example, in accordance with the previously discussed embodiments (FIG. 15) for removal of fluid from the containment jacket 410. By way of example, a syringe may be used to remove air from within the containment jacket 410.

FIG. 23 illustrates inflation of balloon 320 after it has been inserted into the containment jacket 410 in accordance with one embodiment of the present invention. In general, inflation of the balloon 320 should provide pressure on the walls of the cavity 390 to prevent (or reduce) loss of vertebral height. It may be desirable, in certain embodiments, for expansion of the balloon 320 to further increase the height of the vertebral body 170. In certain embodiments, inflation of the balloon 320 may restore some vertebral height lost after the cavity 390 was initially created. As illustrated, the balloon 320 generally may be enclosed within the containment jacket 410. The volume of the balloon 320, when inflated, generally may be smaller than the volume of the containment jacket 410, in accordance with embodiments of the present invention. Furthermore, when inflated, the balloon 320 generally may not occupy the entire volume of the containment jacket 410. By way of example, the balloon 320 may occupy from about 25% to about 90% by volume of the containment jacket 410.

FIG. 24 illustrates introduction of filler material 500 into the containment jacket 410 in accordance with one embodiment of the present invention. As illustrated, the filler material 500 may be introduced into the containment jacket 410 through the inner lumen 340 of the inner catheter 330 of the balloon assembly 280. While not illustrated on FIG. 24, a syringe-type device 510 (shown on FIG. 16) or a needle-type device 540 (shown on FIGS. 17-21) may be used to introduce the filler material 500 through the balloon assembly 280. In general, the filler material 500 may be introduced into the portion of the containment jacket 410 that is not occupied by the balloon 320. In an embodiment, the filler material 500 may fill the portion of the containment jacket 410 that is not occupied by the balloon 320. The containment jacket 410 may expand with the introduction of the filler material 410. The filler material 500 may then be allowed to cure in the containment jacket 410. In an embodiment, the filler material 500 may exert pressure to prevent (or reduce) loss of vertebral height. It may be desirable, in certain embodiments, for the filler material 500 to exert pressure that further increases height of the vertebral body 170. As illustrated, the containment jacket 410 may generally conform to the shape of the cavity 390. It may be desirable, in certain embodiments, for the containment jacket 410 to a complaint balloon (e.g., polyurethane) that can contain the filler material 500 to prevent leakage while permitting interdigitation of the filler material 500 with the cancellous bone 360.

As illustrated by FIG. 25, after the filler material 500 has been allowed to cure, the balloon assembly 280 (shown on FIG. 24) may be removed. With removal of the balloon assembly 280 and, thus, the balloon 320 from within the containment jacket 410, a portion of the containment jacket 410 is not occupied. This unoccupied portion of the containment jacket is represented on FIG. 25 by reference number 630. As illustrated by FIG. 25, an access channel to the unoccupied portion 630 is maintained by tubular member 420 of the containment assembly 400 that is disposed within the cannula 20 of the cannula assembly 10.

Figure 26:
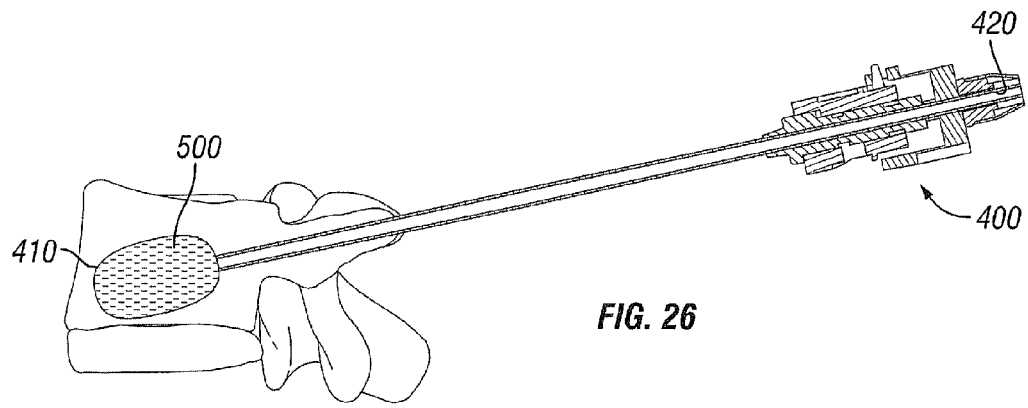
FIG. 26 illustrates introduction of filler material to fill the remainder of a containment jacket placed within a vertebral body in accordance with one embodiment of the present invention.

FIG. 26 illustrates introduction of an additional volume of the filler material 500 into the containment jacket 410. As illustrated, the additional volume of the filler material 500 may be introduced through the tubular member 420 of the containment assembly 400. The additional volume of the fill material may generally fill the unoccupied portion 630 (shown on FIG. 25) of the containment jacket 410 so that the containment jacket 410 is filled with the filler material 500, for example. While not illustrated on FIG. 26, a syringe-type device 510 (shown on FIG. 16) or a needle-type device 540 (shown on FIGS. 17-21) may be used to introduce the additional volume of the filler material 500 through the containment assembly 400. The additional volume of the filler material 500 may then be allowed to cure in the containment jacket 410.

Figure 27:
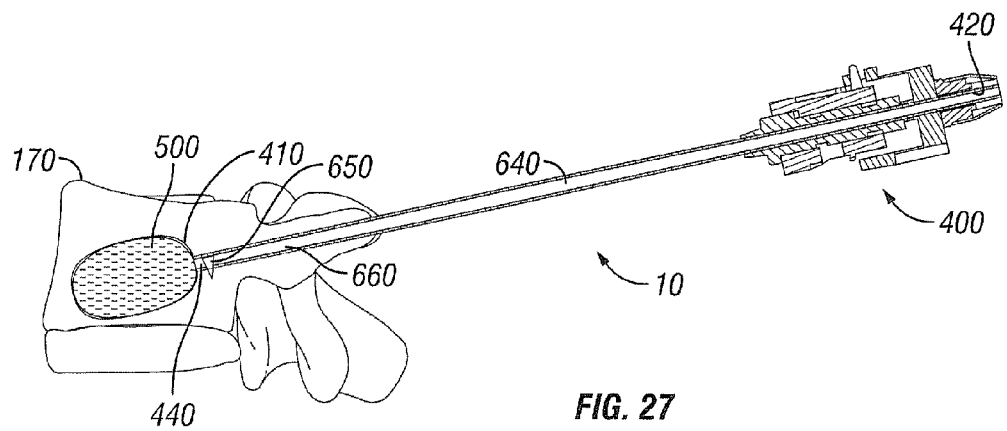
FIG. 27 illustrates detachment of the containment jacket from a containment assembly in accordance with one embodiment of the present invention.

Embodiments of the present invention further may include detaching the containment jacket 410 from the containment assembly 400. FIG. 27 illustrates removal of the containment jacket 410 in accordance with one embodiment of the present invention. As previously mentioned, the containment jacket 410 may be attached to the distal end 440 of the tubular member 420. As illustrated, a cutting device 640 having a cutting mechanism 650 in its distal end 660 may be inserted into the tubular member 420. The cutting device 640 may then be used to detach the containment jacket 410, leaving the containment jacket 410 within the vertebral body 170. In another embodiment, the containment jacket 410 is provided with a perforated line detachment mechanism so that the containment jacket 410 can be detached and maintained within the vertebral body. Once the containment jacket 410 has been detached, the containment assembly 400 and the cannula assembly 10 may be removed, leaving the containment jacket 410. Accordingly, the containment jacket 410 containing the filler material 500 may be left within the vertebral body 170.

Figure 28:
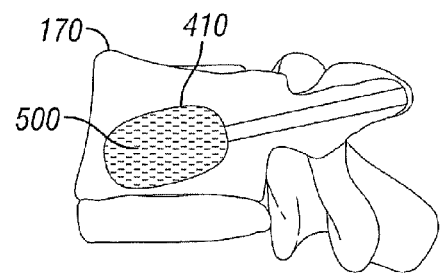
FIG. 28 illustrates a containment jacket placed within a vertebral body, the containment jacket containing a filler material, in accordance with one embodiment of the present invention.

FIG. 28 illustrates a containment jacket 410 within a vertebral body 170 and containing a filler material 500 in accordance with one embodiment of the present invention. In an embodiment (FIGS. 15 and 16), the filler material 500 may be introduced directly into the containment jacket 410. In an alternative embodiment (FIGS. 22-27), a balloon assembly 280 may be used while introducing the filler material 500 into the containment jacket 410. In an embodiment, the filler material 500 may exert pressure to prevent (or reduce) loss of vertebral height.

The preceding description describes the use of a filler material 500 in accordance with embodiments of the present invention. Those of ordinary skill in the art will appreciate that the filler material 500 may comprise any of a variety of materials that may be utilized to, for example, fill and stabilize the cavity 390 in the vertebral body 170. Examples of suitable materials may include bone cements (e.g. polymethyl methacrylate), human bone graft and synthetic derived bone substitutes.

In addition, the preceding description is directed, for example, to treatment of vertebral fractures that includes a containment assembly for cement containment and/or a balloon assembly for maintaining vertebral height. It should be understood that the present technique also may be used in other suitable bone treatments were maintenance of vertebral height and/or cement containment may be desired. By way of example, embodiments of the present invention may be used to treat tibia plateau fractures, distal radius fractures, and cancelleous fractures.

While it is apparent that the invention disclosed herein is well calculated to fulfill the objects stated above, it will be appreciated that numerous modifications and embodiments may be devised by those skilled in the art.

What is claimed is:

1. A method for treating a bone comprising:
   inserting a cannula having an inner lumen into the bone;
   creating a cavity in the bone;
   providing a containment assembly comprising:
     a tubular member having a proximal end and a distal end,
     a containment jacket disposed on the distal end of the tubular member, and
     a guide wire disposed through the tubular member with the guide wire extending into the containment jacket;
   inserting the containment jacket through the inner lumen of the cannula and into the cavity;
   inserting a balloon into the containment jacket after insertion of the containment jacket into the cavity and inflating the balloon; and
   introducing a filler material directly in contact with the containment jacket, wherein the filler material is introduced into the containment jacket while the balloon is inflated,
   wherein the containment jacket is an expandable implant, and
   wherein the containment jacket has a proximal end and a distal end, wherein the proximal end of the containment jacket is closer to the distal end of the tubular member than the distal end of the containment jacket, wherein the balloon is inflated near the proximal end of the containment jacket.

2. The method of claim 1 wherein the cannula is inserted through a pedicle and into the bone.

3. The method of claim 1 comprising:
inserting a needle assembly through an incision in a patient's back and into the bone; disposing a guide wire through the needle assembly and into the bone;
removing the needle assembly; and
inserting the cannula over the guide wire and into the bone.

4. The method of claim 1 comprising inserting a drill into the bone through the inner lumen of the cannula and creating a channel in the bone.

5. The method of claim 1 wherein creating the cavity comprises inflating a balloon in the bone.

6. The method of claim 1 wherein the filler material comprises a bone cement.

7. The method of claim 1 comprising removing fluid from the containment jacket after insertion of the containment jacket into the cavity.

8. The method of claim 1 comprising:
deflating the balloon;
removing the balloon from the containment jacket; and
introducing an additional volume of the filler material into the containment jacket after removal of the balloon.

9. The method of claim 1 comprising detaching the containment jacket from the tubular member.

10. The method of claim 1, wherein the balloon includes a lumen therethrough with an exit port at the lumen's distal end that extends beyond the balloon, wherein the filler material is introduced through the exit port into the containment jacket.

11. The method of claim 1, wherein the balloon is in an inflated state near the proximal end of the containment jacket while filler material is introduced more distally in the containment jacket.

12. The method of claim 1, wherein filler material is introduced into an unoccupied portion of the containment jacket while the balloon is in an inflated state near the proximal end of the containment jacket.

13. A method for treating a bone comprising:
inserting a cannula having an inner lumen into the bone;
creating a cavity in the bone;
providing a containment assembly comprising:
a tubular member having a proximal end and a distal end,
a containment jacket disposed on the distal end of the tubular member, and
a guide wire disposed through the tubular member with the guide wire extending into the containment jacket;
inserting the containment jacket through the inner lumen of the cannula and into the cavity;
inserting a balloon into the containment jacket after insertion of the containment jacket into the cavity and inflating the balloon; and
introducing a filler material directly in contact with the containment jacket, wherein the filler material is introduced into the containment jacket while the balloon is inflated
wherein the containment jacket is a compliant balloon,
wherein the containment jacket has a proximal end and a distal end, wherein the proximal end of the containment jacket is closer to the distal end of the tubular member than the distal end of the containment jacket, wherein the balloon is inflated near the proximal end of the containment jacket.

14. The method of claim 13, wherein the balloon includes a lumen therethrough with an exit port at the lumen's distal end that extends beyond the balloon, wherein the filler material is introduced through the exit port into the containment jacket.

\* \* \* \* \*